(12) United States Patent
Ye

(10) Patent No.: US 9,593,125 B2
(45) Date of Patent: Mar. 14, 2017

(54) HETEROCYCLIC FLAVONE DERIVATIVES, COMPOSITIONS, AND METHODS RELATED THERETO

(71) Applicant: EMORY UNIVERSITY, Atlanta, GA (US)

(72) Inventor: Keqiang Ye, Lilburn, GA (US)

(73) Assignee: Emory University, Atlanta, GA (US)

(*) Notice: Subject to any disclaimer, the term of this patent is extended or adjusted under 35 U.S.C. 154(b) by 0 days.

(21) Appl. No.: 14/410,756

(22) PCT Filed: Jul. 25, 2013

(86) PCT No.: PCT/US2013/052030
§ 371 (c)(1),
(2) Date: Dec. 23, 2014

(87) PCT Pub. No.: WO2014/018741
PCT Pub. Date: Jan. 30, 2014

(65) Prior Publication Data
US 2015/0191481 A1    Jul. 9, 2015

Related U.S. Application Data

(60) Provisional application No. 61/676,483, filed on Jul. 27, 2012, provisional application No. 61/694,997, filed on Aug. 30, 2012, provisional application No. 61/715,985, filed on Oct. 19, 2012, provisional application No. 61/776,029, filed on Mar. 11, 2013.

(51) Int. Cl.
| | |
|---|---|
| *C07D 491/052* | (2006.01) |
| *A61K 45/06* | (2006.01) |
| *C07D 491/06* | (2006.01) |
| *A61K 31/353* | (2006.01) |
| *C07D 311/30* | (2006.01) |
| *A61K 31/4188* | (2006.01) |

(52) U.S. Cl.
CPC .......... *C07D 491/06* (2013.01); *A61K 31/353* (2013.01); *A61K 31/4188* (2013.01); *A61K 45/06* (2013.01); *C07D 311/30* (2013.01); *C07D 491/052* (2013.01)

(58) Field of Classification Search
CPC ... C07D 491/06; C07D 491/052; A61K 45/06
USPC .................. 548/302.1; 514/211.13
See application file for complete search history.

(56) References Cited

U.S. PATENT DOCUMENTS

| | | |
|---|---|---|
| 9,029,561 B2 | 5/2015 | Ye |
| 2002/0198248 A1 | 12/2002 | Kelly |
| 2003/0125264 A1 | 7/2003 | Malik |
| 2004/0063665 A1 | 4/2004 | Bargiotti |
| 2004/0198750 A1 | 10/2004 | Green et al. |
| 2006/0025337 A1 | 2/2006 | Sinclair |
| 2006/0111435 A1 | 5/2006 | Sinclair |
| 2011/0144196 A1 | 6/2011 | Ye |
| 2015/0174107 A1 | 6/2015 | Ye |

FOREIGN PATENT DOCUMENTS

| | | |
|---|---|---|
| EP | 0341104 | 11/1989 |
| EP | 0556720 | 11/1993 |
| EP | 0638566 | 2/1995 |
| EP | 0755928 | 1/1997 |
| WO | 9505169 | 2/1995 |
| WO | 0103681 | 1/2001 |
| WO | 2004037193 | 5/2004 |
| WO | 2006001665 | 1/2006 |
| WO | 2008011538 | 1/2008 |
| WO | 2008091710 | 7/2008 |
| WO | 2009003147 | 12/2008 |
| WO | 2010011836 | 1/2010 |
| WO | 2010014613 | 2/2010 |
| WO | 2011156479 | 12/2011 |
| WO | WO 2011-156479 | * 12/2011 |

OTHER PUBLICATIONS

Akama et al. "Structure-Activity Relationships of the 7-Substituents of 5,4'-Diamino-6,8,3'-trifluoroflavone, a Potent Antitumor Agent" J. Med. Chem., 1998; 41: 2056-2067.
Anjaneyulu et al. "Antidepressant Activity of Quercetin, a Bioflavonoid in Streptozotocin-Induced Diabetic Mice" J Med Food, 2003; 6(4): 391-395.
Berge et al. "Pharmaceutical Salts" J Pharm Sci., 1977; 66(1): 1-18.
Jang et al. "A Selective TrkB agonist with potent neurotrophic activities by 7,8-dihydroxyflavone" PNAS, 2010; 107(6): 2687-2692.
Kato et al. "Studies of Organo Sulfur Compounds" Bull Chem Soc Japan, 1973; 46(3): 860-863.
Liu et al. "A synthetic 7,8-dihydroxyflavone derivative promotes neurogeneisis and exhibits potent antidepressant affect" J. Med. Chem., 2010; 53: 8274-8286.
Liu et al. "O-Methylated Metabolite of 7,8-Dihydroxyflavone Activates TrkB Receptor and Displays Antidepressant Activity" Pharmacology, 2013; 91(3-4): 185-200.
Loaiza-Perez "Aryl Hydrocarbon Receptor Mediates Sensitivity of MCF-7 Breast Cancer Cells to Antitumor Agent 2-(4-Amino-3-methylphenyl) Benzothiazole" Molecular Pharmacology, 2002; 61(1): 13-19.

(Continued)

*Primary Examiner* — Rita Desai
(74) *Attorney, Agent, or Firm* — Emory Patent Group

(57) ABSTRACT

In certain embodiments, the disclosure relates to heterocyclic flavone derivatives, such as those described by formula provided herein, pharmaceutical compositions, and methods related thereto. In certain embodiments, the disclosure relates to methods of 5 treating or preventing diseases or conditions related to BDNF and TrkB activity, such as depression, stroke, Rett syndrome, Parkinson's disease, and Alzheimer's disease by administering effective amounts of pharmaceutical compositions comprising compounds disclosed herein to a subject in need thereof.

4 Claims, 16 Drawing Sheets

(56) References Cited

OTHER PUBLICATIONS

Soural et al. "2-Phenyl substituted-3-Hydroxyquinolin-4(1H)-one-Carboxamides: Structure-Cytotoxic Activity Relationship Study" ACS Comb. Sci., 2011; 13: 39-44.
Yilmaz et al. "4D-QSAR Study of p56lck Protein Tyrosine Kinase Inhibitory Activity of Flavonoid Derivatives Using MCET Method" Bull. Korean Chem. Soc., 2011; 32(12): 4352-4360.
Extended European Search Report for EP Application No. 13822110.6, Dated Feb. 23, 2016.

\* cited by examiner

HETEROCYCLIC FLAVONE DERIVATIVES, COMPOSITIONS, AND METHODS RELATED THERETO

CROSS-REFERENCE TO RELATED APPLICATIONS

This application is the National Stage of International Application Number PCT/US2013/052030 filed Jul. 25, 2013, which claims priority to U.S. Provisional Application No. 61/676,483 filed Jul. 27, 2012, U.S. Provisional Application No. 61/694,997 filed Aug. 30, 2012, U.S. Provisional Application No. 61/715,985 filed Oct. 19, 2012, and U.S. Provisional Application No. 61/776,029 filed Mar. 11, 2013. The entirety of each of these applications is hereby incorporated by reference for all purposes.

STATEMENT REGARDING FEDERALLY SPONSORED RESEARCH OR DEVELOPMENT

This invention was made with government support under Grant No. DC010204 awarded by the National Institutes of Health. The government has certain rights in the invention.

FIELD

In certain embodiments, the disclosure relates to heterocyclic flavone derivatives, such as those described by formula provided herein, pharmaceutical compositions, and methods related thereto. In certain embodiments, the disclosure relates to methods of treating or preventing diseases or conditions related to BDNF and TrkB activity, such as depression, stroke, Rett syndrome, Parkinson's disease, and Alzheimer's disease by administering effective amounts of pharmaceutical compositions comprising compounds disclosed herein to a subject in need thereof.

BACKGROUND

Neurotrophins are growth factors regulate the development and maintenance of the peripheral and the central nervous system. Brain-derived neutrotrophic factor (BDNF) is a member of the neurotrophin family, which includes nerve growth factor (NGF), NT-3 and NT-4/5. BDNF binding to its cognate receptor, TrkB, triggers its dimerzation through conformational changes and autophosphorylation of tyrosine residues, resulting in activation of the three major signaling pathways—mitogen-activated protein (MAPK), phosphatidylinositol 3-kinase (PI3K) and phospholipase C-γ1 (PLC-γ1). Various studies have shown links between BDNF and TrkB to conditions such as depression, schizophrenia, obsessive-compulsive disorder, Alzheimer's disease, Huntington's disease, Rett syndrome, and dementia, as well as anorexia nervosa and bulimia nervosa. See Dwivedi, Neutopsychiatric Disease and Treatment, 2009, 5: 433-49; Xiu et al., Progress in Neuro-Psychopharmacology and Biological Psychiatry, 2009, 33(8):1508-12; Maina et al., Journal of Affective Disorders, 2010, 122(1-2):174-8; Zuccato et al., Nature Reviews Neurology, 2009, 5(6):311-22; Zajac et al., 2010, Hippocampus 20 (5): 621-36; Zeev et al., Neurology, 2009, 72 (14): 1242-7; Arancio et al., 2007, Current Opinion in Neurobiology, 17 (3): 325-30; Mercader et al, Neuropsychobiology, 2007, 56 (4): 185-90; Kaplan et al., International Journal of Eating Disorders, 2008 41 (1): 22-8.

It has been reported that certain 7,8-dihydroxyflavone derivatives promote neurogenesis and exhibits potent antidepressant effects. See Liu et al., J Med Chem, 2010, 53 (23), pp 8274-8286. See also WO/2010/011836, WO/2010/107866, and WO 2011/156479. As 7,8-dihydroxyflavone derivatives are catechol and phenyl containing compounds, they are prone to be cleared in the circulatory system following oxidation, glucuronidation, sulfation or methylation. Thus, there is a need to identify improved flavone derivatives with improved pharmacokinetic properties.

The health benefits of flavonoid compounds have been reported in a number of references, including neuroprotective and anti-cancer properties. See Chiruta et al., 2012, Journal of Medicinal Chemistry, 55, 378-89; Sousa et al., 2012, European Journal of Organic Chemistry, 1, 132-43; Sivakumar et al., PCT Appl. No. US 2010/0179210. Derivatives of 3-hydroxyquinolone compounds have also been previously synthesized with reports of their fluorescence and biological activities disclosed. See Yushchenko et al., 2006, Tetrahedron Letters, 47, 905-8; Krejci et al., PCT Appl. No. US 2010/0022587.

The references cited hereby are not an admission of prior art.

SUMMARY

In certain embodiments, the disclosure relates to heterocyclic flavone derivatives, such as those described by formula provided herein, pharmaceutical compositions, and methods related thereto. In certain embodiments, the disclosure relates to methods of treating or preventing diseases or conditions related to BDNF and TrkB activity, such as depression, stroke, Rett syndrome, Parkinson's disease, and Alzheimer's disease by administering effective amounts of pharmaceutical compositions comprising compounds disclosed herein.

In certain embodiments, the disclosure related to a compound comprising Formula I:

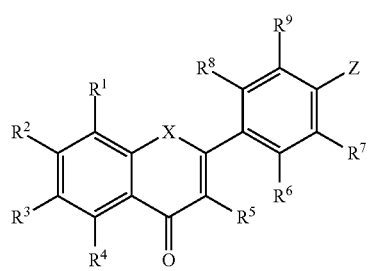

Formula I or salt, prodrug, or ester thereof wherein

X is O, S, or NH;

Z is amino, diaminoalkyl, or heterocyclyl such as pyrrolidinyl optionally substituted with one or more, the same or different, $R^{15}$;

$R^1$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^1$ is optionally substituted with one or more, the same or different, $R^{15}$; or $R^1$ and $R^2$ and attached atoms form a 5 membered heterocyclic ring, such as imidazolyl, optionally substituted with $R^{15}$;

$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;

$R^3$, $R^4$, $R^5$, $R^6$, $R^7$, $R^8$, and $R^9$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, and $R^9$ are optionally substituted with one or more, the same or different, $R^{15}$;

$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to pharmaceutical compositions comprising compounds disclosed herein and a pharmaceutically acceptable excipient. In certain embodiments, the pharmaceutical composition is in the form of a tablet, capsule, pill, or solution for injection.

In certain embodiments, the disclosure relates to methods of preventing or treating a BDNF and TrkB related disease or condition comprising the administering an effective amount of a pharmaceutical composition disclosed herein, to a subject in need thereof. In some embodiments, the subject is diagnosed with, exhibiting symptoms of, or at risk of the disease or condition. In some embodiments, the disease or condition is depression, schizophrenia, obsessive-compulsive disorder, anorexia nervosa, bulimia nervosa, anxiety, amyotrophic later sclerosis, Alzheimer's disease, Huntington's disease, Rett syndrome, epilepsy, Parkinson's disease, dementia, diabetic neuropathy, peripheral neuropathy, obesity, peripheral nerve injury, pain, or stroke.

In certain embodiments, the disease is depression and the pharmaceutical composition is administered in combination with an anti-depressant such as a selective serotonin reuptake inhibitor such as citalopram, escitalopram, fluoxetine, fluvoxamine, paroxetine, sertraline, or vilazodone, a serotonin-norepinephrine reuptake inhibitor such as desvenlafaxine, duloxetine, milnacipran, venlafaxine, a noradrenergic and specific serotonergic antidepressant such as mianserin and mirtazapine, a norepinephrine reuptake inhibitor such as atomoxetine, mazindol, reboxetine, viloxazine, a norepinephrine-dopamine reuptake inhibitor such as bupropion, a selective serotonin reuptake enhancer such as tianeptine and amineptine, a norepinephrine-dopamine disinhibitor such as agomelatine, a tricyclic antidepressant such as amitriptyline, clomipramine, doxepin, imipramine, trimipramine, desipramine, nortriptyline, protriptyline, a monoamine oxidase inhibitor such as isocarboxazid, moclobemide, phenelzine, selegiline, tranylcypromine.

In some embodiments, the disclosure relates to the use of a compound disclosed herein in the production of a medicament for the treatment or prevention of a BDNF and TrkB related disease or condition.

***P<0.0001 vs vehicle). E. TrkB but not TrkA is activated by compound m and i in mouse brain. The brain lysates from above chronically treated mice were analyzed by immunoblotting with anti-p-TrkA 794 and p-TrkB 816.

Figure 4:
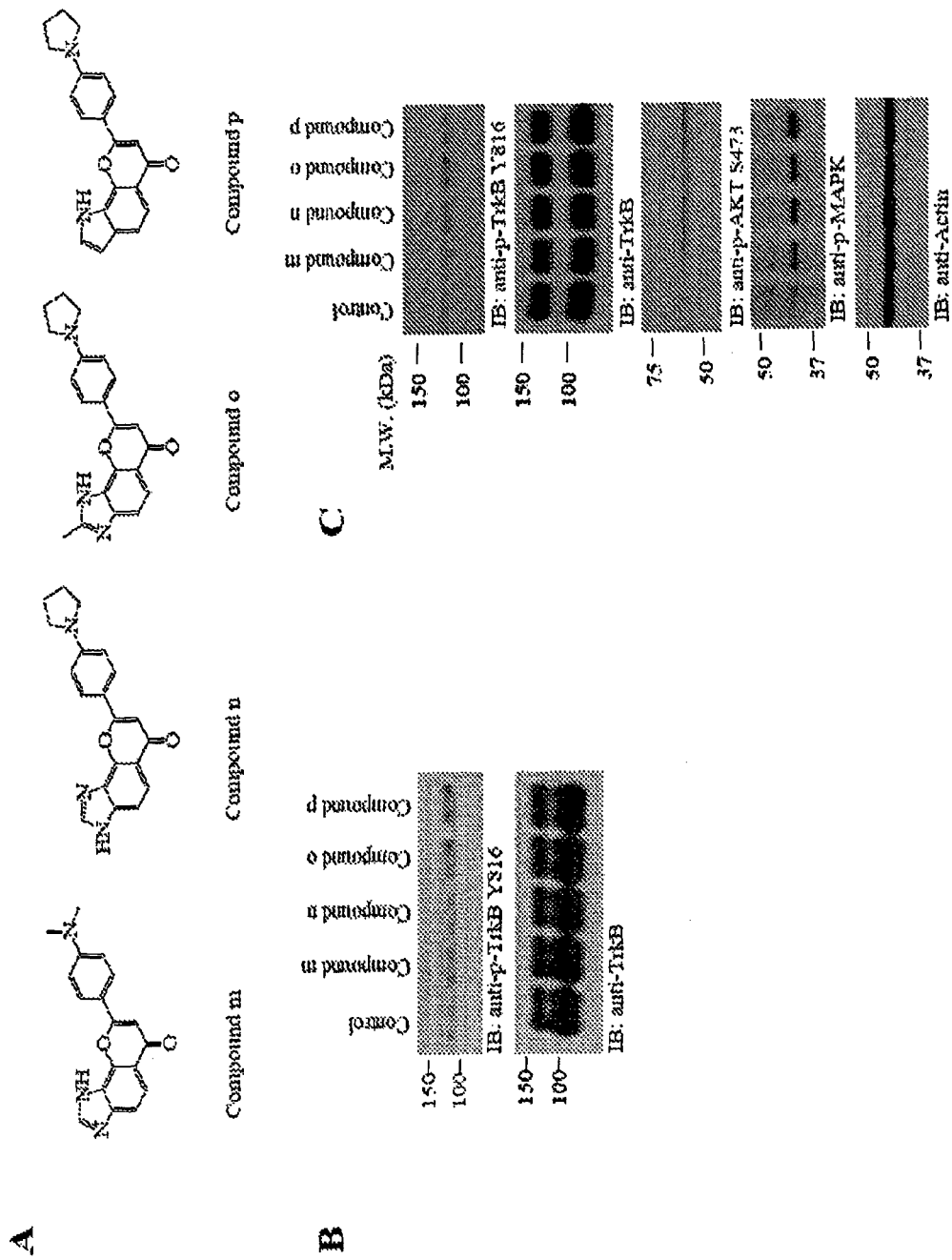

FIG. 4 shows data indicating 4'-pyrrolidino-7,8-methyl-imidazole-flavone triggers TrkB activation in primary neurons and mouse brain. A, Chemical structures of various synthetic 4'-pyrrolidino-flavone derivatives. B, 4'-pyrrolidino-7,8-methyl-imidazole-flavone triggers TrkB activation in primary neurons. Rat primary neurons were treated with 500 nM various indicated compounds from 15 min. The neuronal lysates (20 mg) were analyzed with various antibodies. C, 4'-pyrrolidino-7,8-methyl-imidazole-flavone triggers TrkB activation in mouse brain. One mg/kg of various indicated compounds were orally administrated into C57 BL/6J mice and TrkB phosphorylation (top panel) and its downstream signaling cascades including Akt and MAPK in the hippocampus of mouse brain were analyzed by immunoblotting at 2 h. The downstream p-Akt and p-MAPK activity coupled to the TrkB activation patterns ($3^{rd}$ and $4^{th}$ panels).

Figures 1, 5:
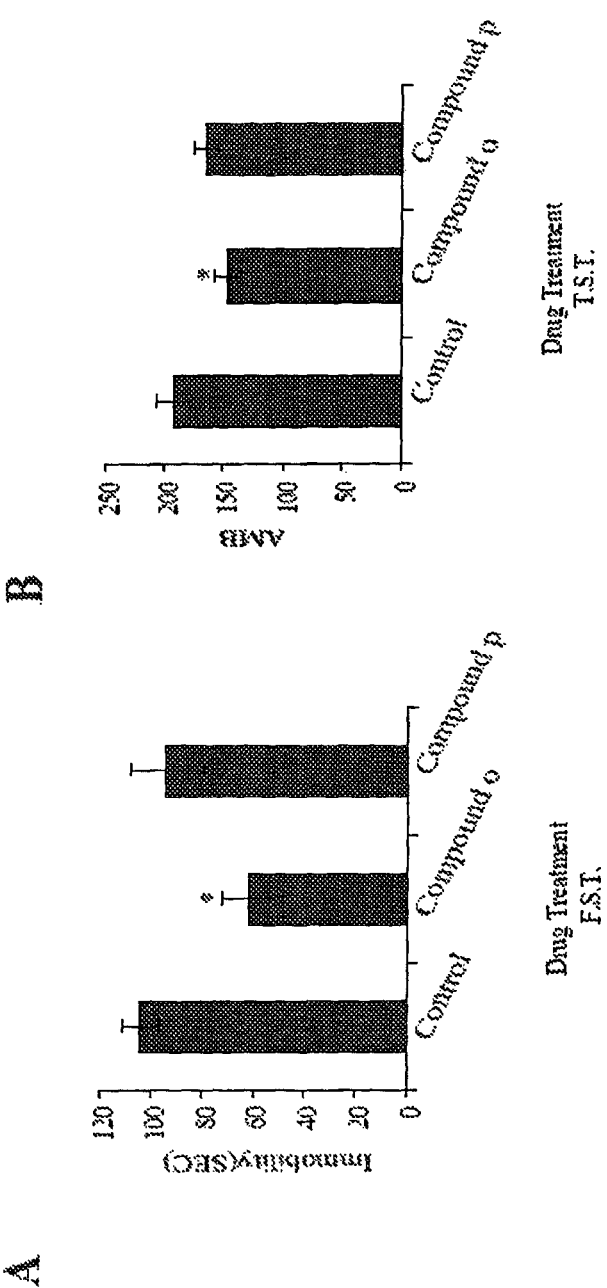
Figures 2, 5:
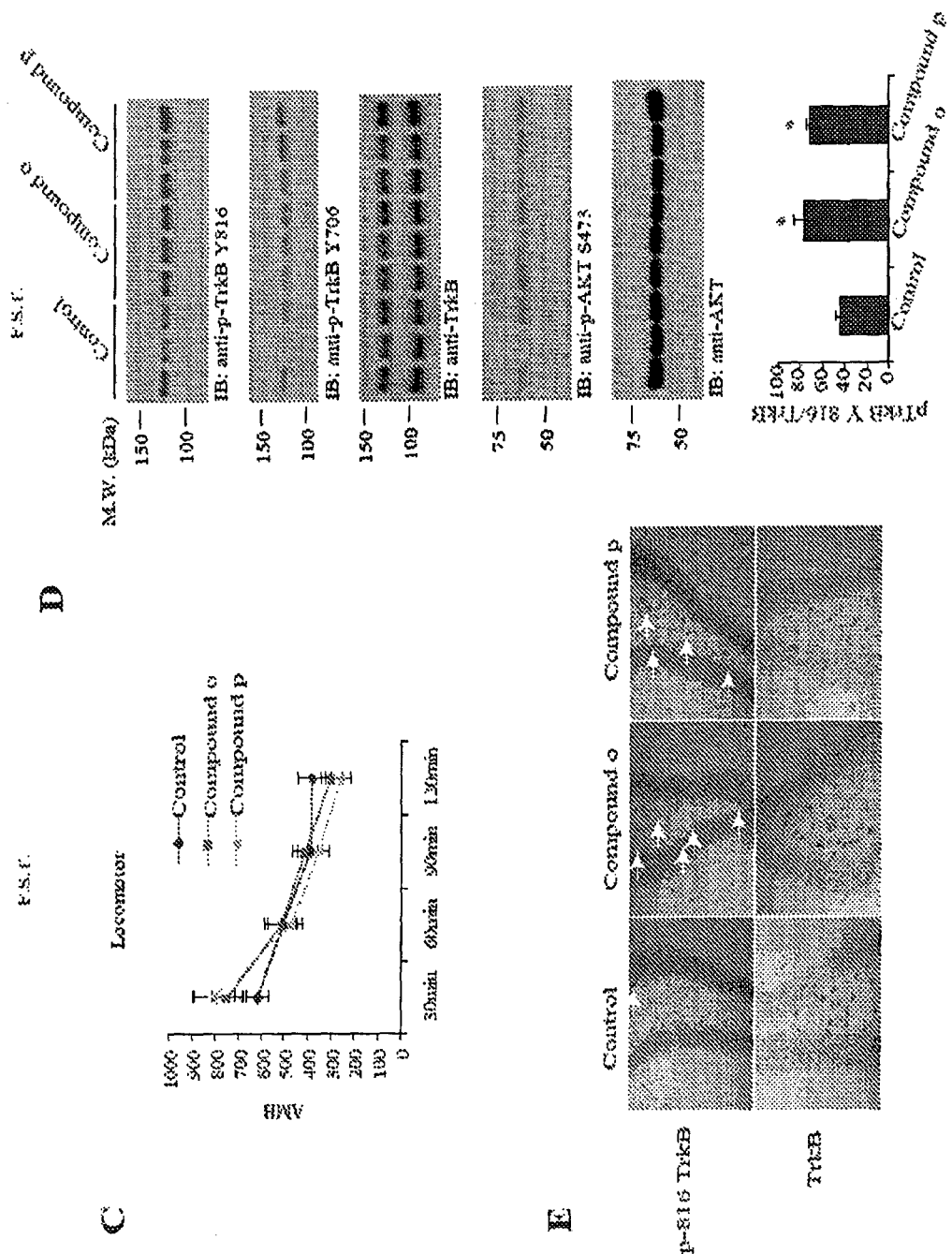

FIG. 5 shows data indicating 4'-pyrrolidino-7,8-methyl-imidazole-flavone triggers TrkB activation in mouse brain and exhibits antidepressant effect. A, Forced swim test. Male C57BL/6J mice (8 mice/group) were orally administrated by gavage with 2.5 mg/kg compound o or compound p and vehicle solvent saline for 21 days and subjected to a forced swim test (6 min, immobility recorded in the last 4 min). Compound o but not compound p significantly decreased the immobility. Data are presented as mean±SEM. Analysis of variance (ANOVA) revealed significant difference between vehicle and either compound m or compound i (n=8, *P<0.0001 vs vehicle). B, Tail suspension test. The drug-treated mice were subjected tail suspension assay. Compound o but not p reduced the immobility. Data are presented as mean±SEM. Analysis of variance (ANOVA) revealed significant difference between vehicle and either compound m or compound i (n=8, *P<0.0001 vs vehicle). C. Locomotor activity assay. Neither of the tested compounds altered locomotor activity. D. Both compound o and p activate TrkB and its downstream signaling cascades. 2.5 mg/kg of various indicated compounds were orally administrated into C57 BL/6J mice and TrkB phosphorylation and its downstream effector Akt activation in the hippocampus of mouse brain were analyzed by immunoblotting after behavioral tests. Both compound o and p evidently elevated TrkB phosphorylation (upper panels). The downstream p-Akt activity was also upregulated by compound o and p (4th panel). The quantitative ratio of P-TrkB/total TrkB in drug-treated mouse brain was analyzed (bottom panel) (***, P<0.001 vs control; Student's t test). The data were from two sets of replicated experiments (mean±SEM). E, Immunohistochemistry assay. Both compound o and p elevated TrkB phosphorylation in hippocampus. The chronic drug-treated mice were perfumed and the brain sections were stained with anti-p-TrkB 816 and anti-TrkB antibodies. The p-TrkB activated neurons were labeled with white arrows.

Figures 1, 6:
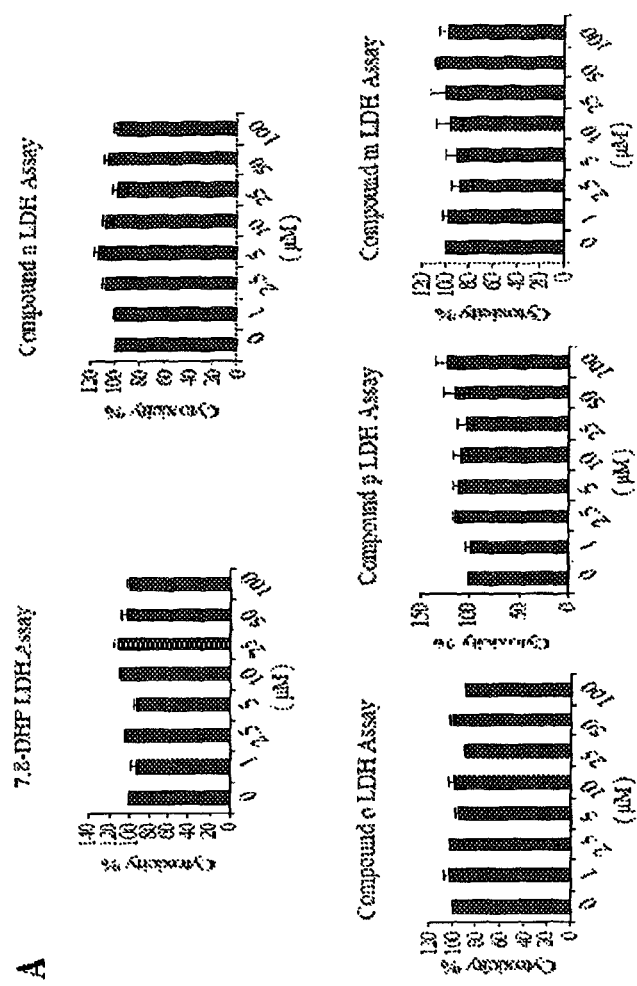
Figures 2, 6:
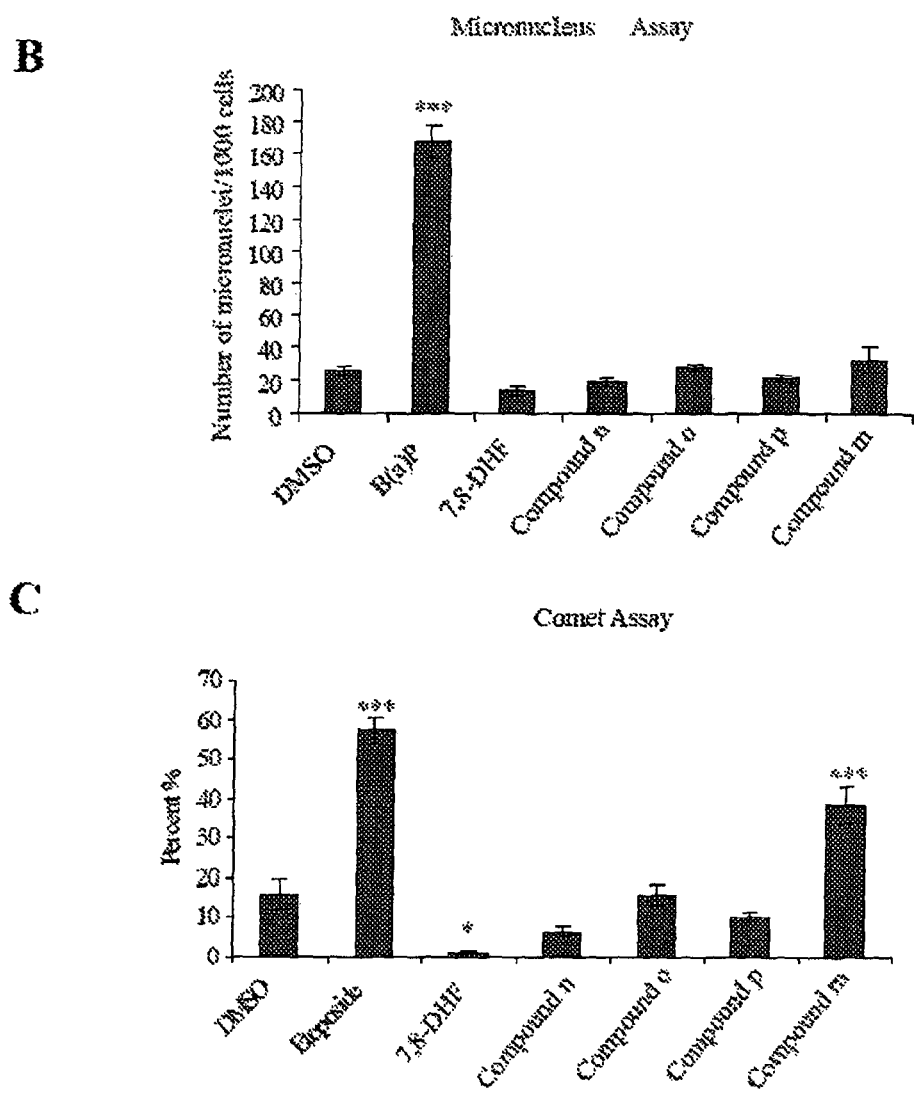

FIG. 6 shows data on in vitro cytotoxicity and genotoxicity assay. A, Cytotoxicity assay with hepatocyte HepG2 cells. HepG2 cells were treated with various concentrations of flavonoids for 24 h. The drug-treated cells were subjected to trypan blue exclusive assay. Data are presented as mean±SEM. (n=3, *P<0.0001 vs vehicle). B, Micronuclei assay with hepatocyte HepG2 cells. HepG2 cells were treated with 50 µM of various compounds for 24 h. The nuclei were stained with DAPI. Data are presented as mean±SEM. (n=3, *P<0.0001 vs vehicle). C, Comet assays. HepG2 cells were treated with 100 µM of various compounds for 24 h. The percentage of lesion DNA in tail was used as a parameter for measurement of DNA damage. Data are presented as mean±SEM. (n=3, ***P<0.0001 vs vehicle, One-way ANOVA).

Figure 7:
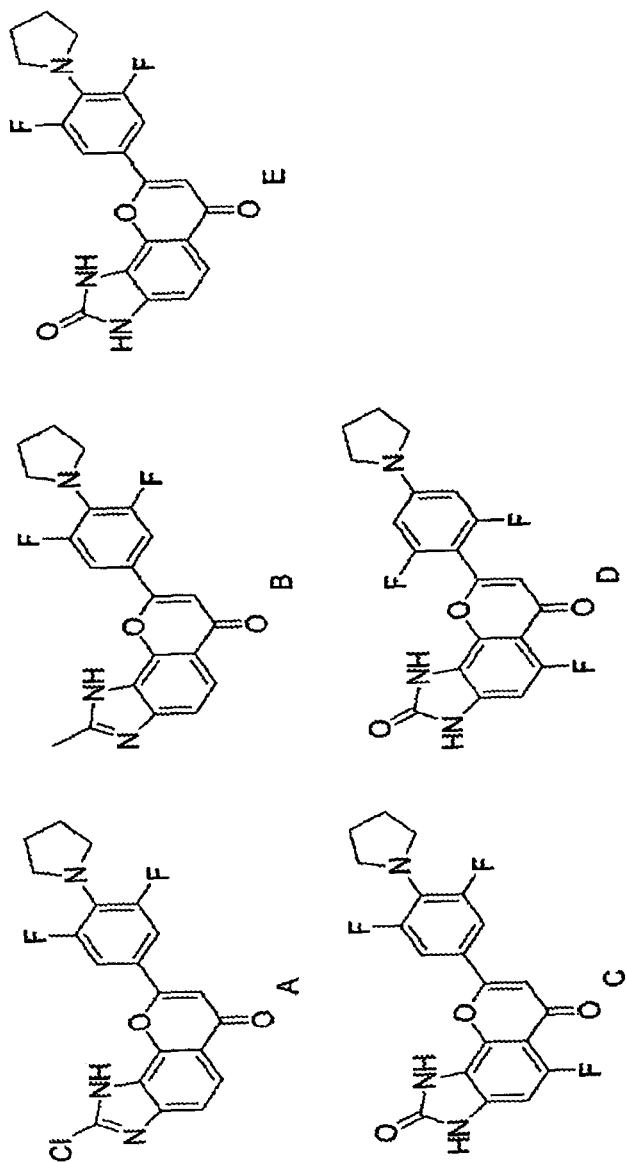

FIG. 7 illustrates certain embodiments of the disclosure.

Figure 8A:
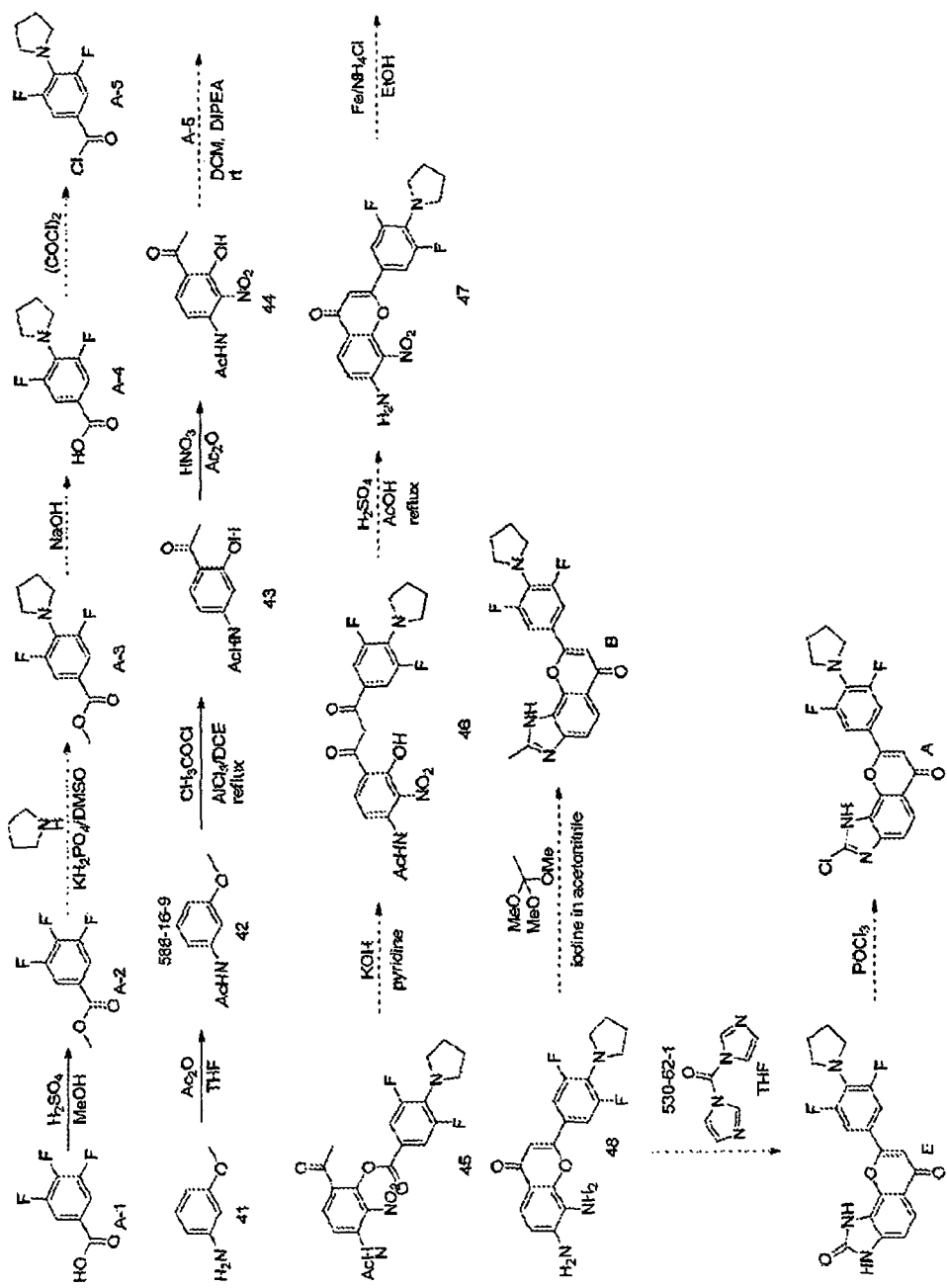

FIG. 8A illustrates methods of preparing certain embodiments of the disclosure.

Figure 8B:
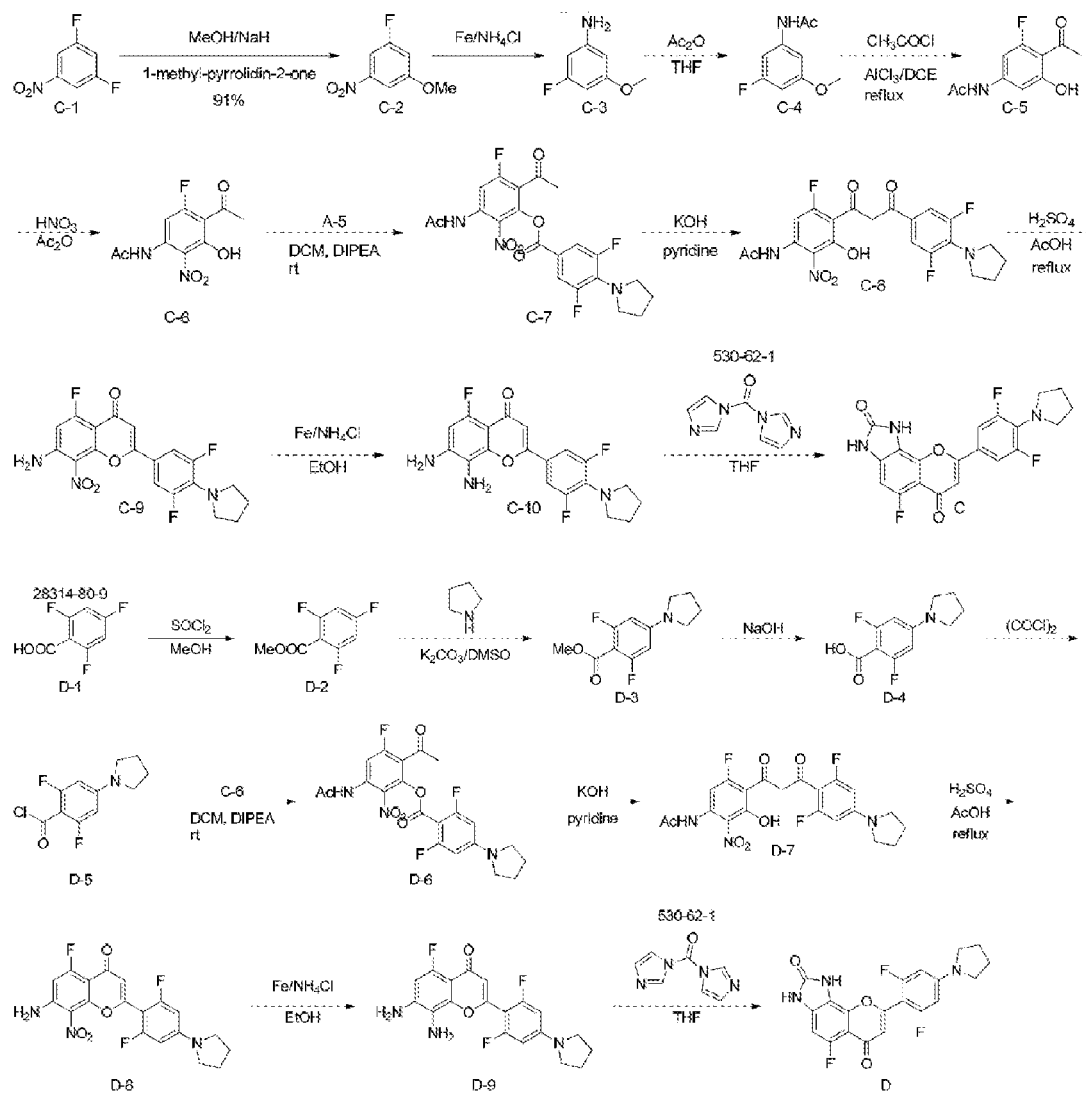

FIG. 8B illustrates methods of preparing certain embodiments of the disclosure.

Figure 8C:
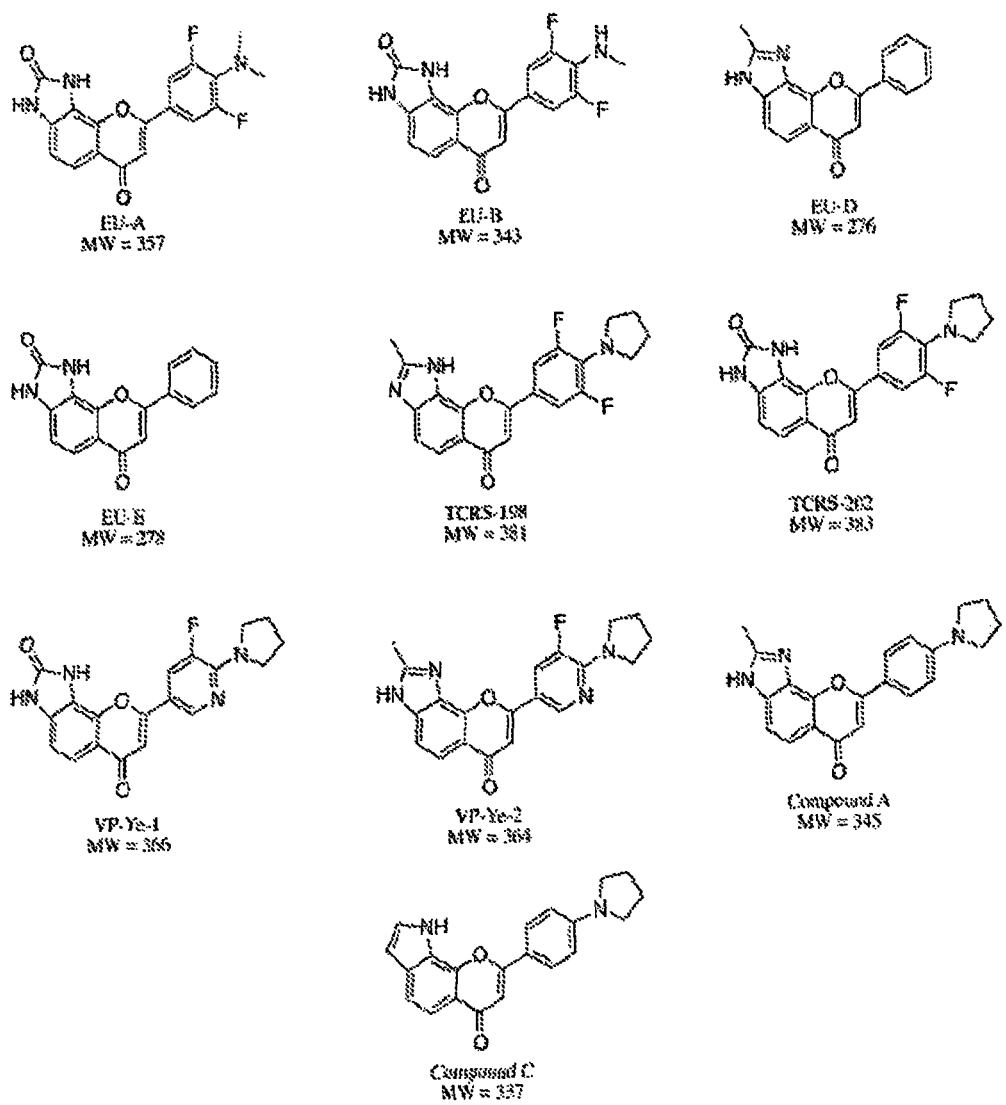

FIG. 8C certain embodiments of the disclosure.

Figure 9:
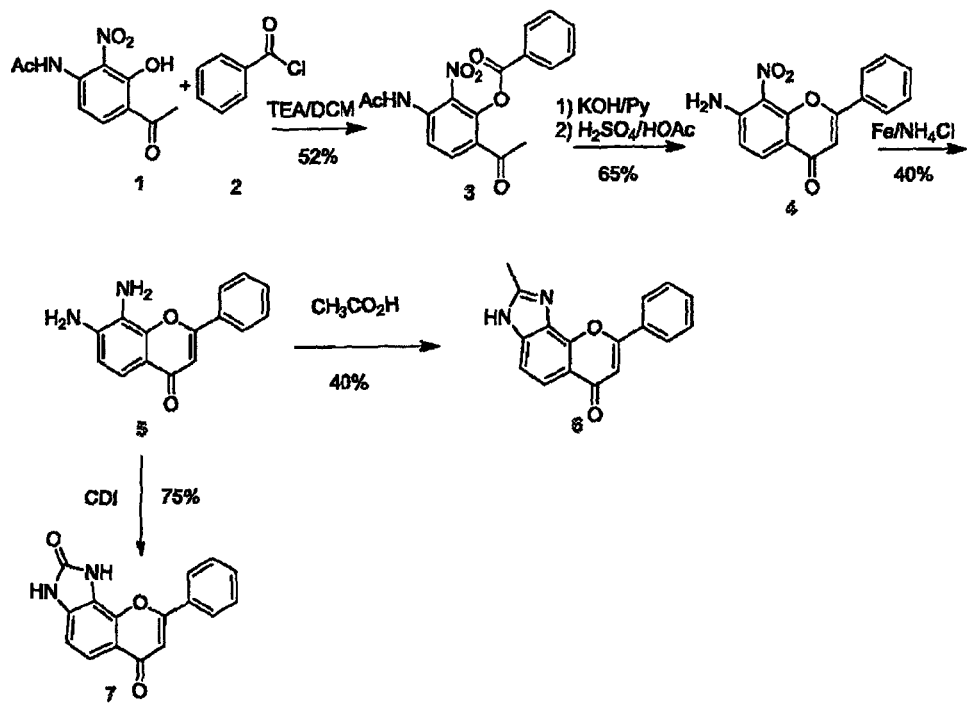

FIG. 9 illustrates methods of preparing certain embodiments of the disclosure.

Figure 10:
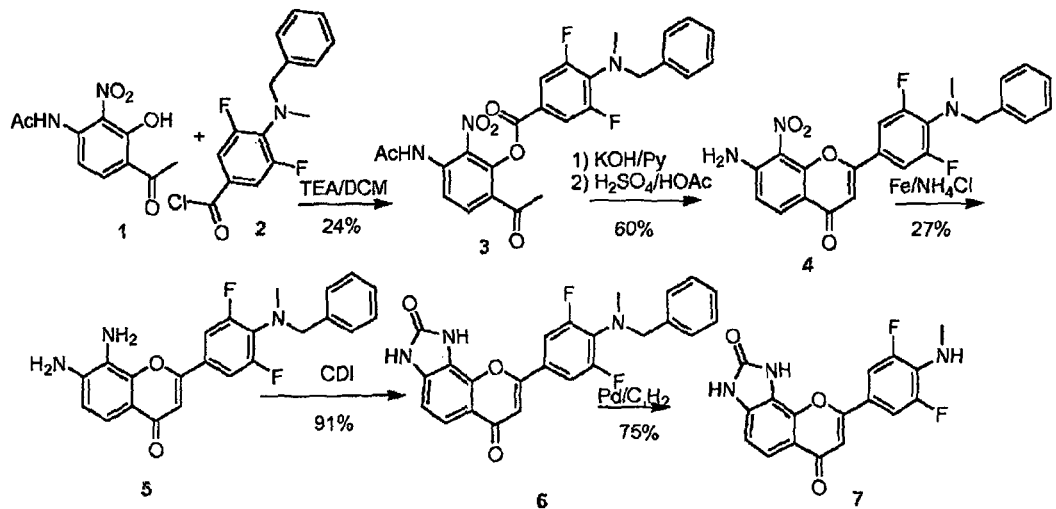

FIG. 10 illustrates methods of preparing certain embodiments of the disclosure.

Figure 11:
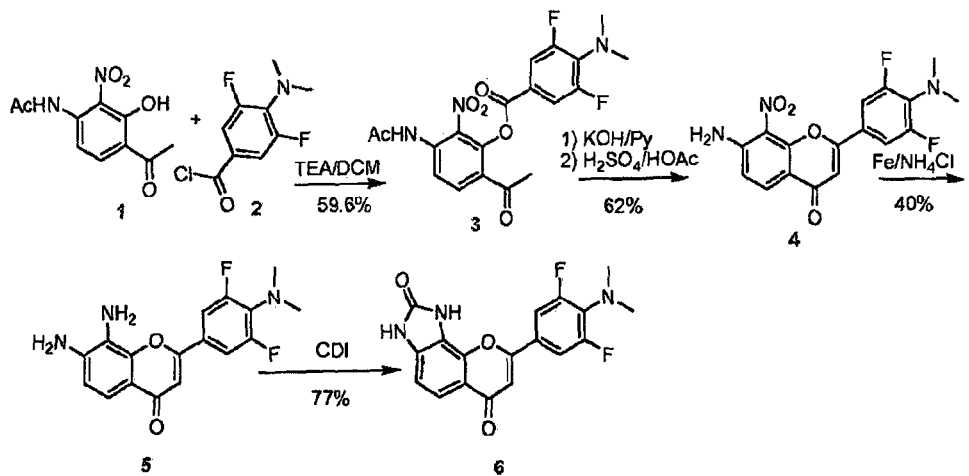

FIG. 11 illustrates methods of preparing certain embodiments of the disclosure.

Figure 12:
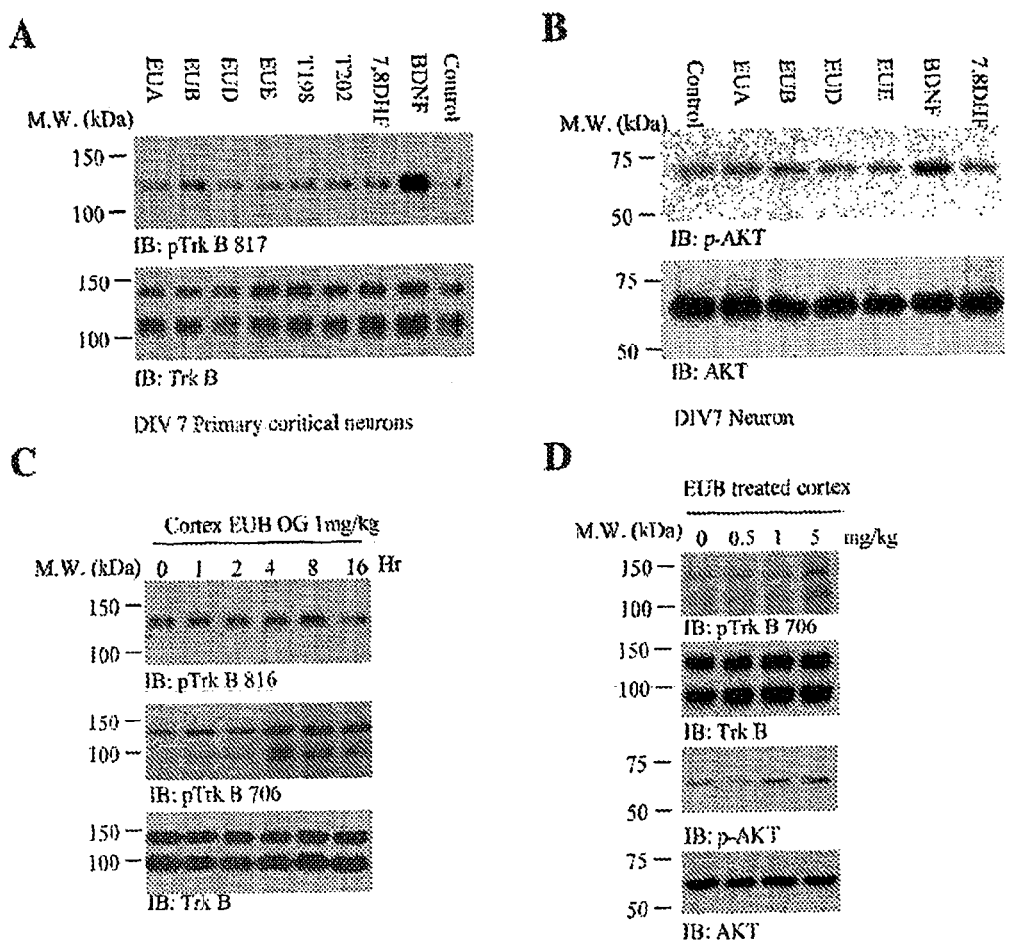

FIG. 12 shows data on 7,8-DHF derivatives to activate TrkB in primary neuronal cultures and in mouse brain after oral administration. A & B. Synthetic compound EUB robustly activates TrkB and Akt in DIV 7 primary cortical neurons. 500 nM of different synthetic compounds were added to DIV 7 neurons for 15 min. The cell lysates were analyzed by immunoblotting with indicated p-TrkB 817 and p-Akt 473 antibodies, respectively. C. EUB provokes TrkB activation in mouse brain in time-dependent manner. 1 mg/kg of EUB was orally injected into C57/BL6 mice and mouse brain was harvested at different time points and TrkB phosphorylation status was analyzed by immunoblotting. TrkB was activated at 1 h and peaked at 4 h. D. EUB activates TrkB in a dose-dependent manner.

DETAILED DISCUSSION

Terms

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Embodiments of the present disclosure will employ, unless otherwise indicated, techniques of synthetic organic chemistry, biochemistry, biology, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used herein a "flavone" refers to any compound comprising a 2-phenyl-4H-chromen-4-one ring system.

As used herein, "alkyl" means a noncyclic straight chain or branched, unsaturated or saturated hydrocarbon such as those containing from 1 to 10 carbon atoms, typically 1 to 6 carbon atoms. Within any embodiments, herein alkyl may refer to an alkyl with 1 to 6 carbons ($C_{1-6}$alkyl). Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—$CH_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—$CH_3$).

"Alkyloxycarbonyl" refers to an alkyl as defined above attached through a carboxy bridge (i.e., —(C=O)Oalkyl.

"Alkylcarbamoyl" refers to an alkyl as defined above attached through a carbonyl bridge (i.e., —(C=O)NHalkyl).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfonamide" refers to an alkyl as defined above attached through a sulfamoyl bridge (i.e., —S(=O)$_2$NHalkyl), and an "Arylsulfonamide" refers to an alkyl attached through a sulfamoyl bridge (i.e., (i.e., —S(=O)$_2$NHaryl).

"Alkylsulfinyl" refers to an alkyl as defined attached through a sulfinyl bridge (i.e. —S(=O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —$NR_aR_b$, —$NR_aC(=O)R_b$, —$NR_aC(=O)NR_aNR_b$, —$NR_aC(=O)OR_b$, —$NR_aSO_2R_b$, —$C(=O)R_a$, —$C(=O)OR_a$, —$C(=O)NR_aR_b$, —$OC(=O)NR_aR_b$, —$OR_a$, —$SR_a$, —$SOR_a$, —$S(=O)_2R_a$, —$OS(=O)_2R_a$ and —$S(=O)_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulphur atom or replacing an amino group with a hydroxyl group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Compounds

In certain embodiments, the disclosure relates to compounds of Formula I:

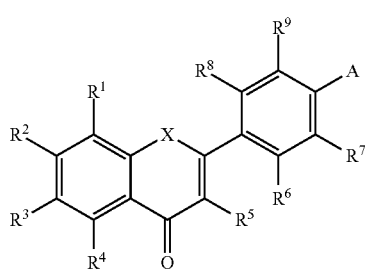

Formula I or salt, prodrug, or ester thereof wherein
X is O, S, or NH;
A is amino, diaminoalkyl, or heterocyclyl such as pyrrolidinyl optionally substituted with one or more, the same or different, $R^{15}$;
$R^1$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^1$ is optionally substituted with one or more, the same or different, $R^{15}$; or $R^1$ and $R^2$ and attached atoms form a 5 membered heterocyclic ring, such as imidazolyl optionally substituted with $R^{15}$;

$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;

$R^3$, $R^4$, $R^5$, $R^6$, $R^7$, $R^8$, and $R^9$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, and $R^9$ are optionally substituted with one or more, the same or different, $R^{15}$;

$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is O.
In certain embodiments, A is pyrrolidinyl.
In certain embodiments, $R^1$ and $R^2$ form imidazolyl or indolyl.
In certain embodiments, $R^7$ and $R^9$ are a halogen, one of or both.
In certain embodiments, $R^6$ and $R^8$ are a halogen, one of or both.
In certain embodiments, $R^4$ is a halogen, e.g., halogen is fluoro.
In certain embodiments, A is a nonaromatic heterocyclyl bond to the phenyl ring through a nitrogen heteroatom.
In certain embodiments, the disclosure relates to compounds of Formula IA:

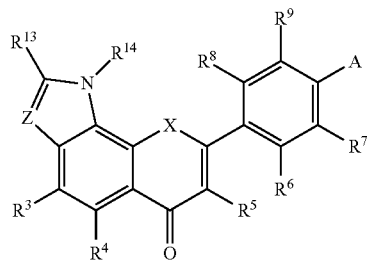

Formula IA or salt, prodrug, or ester thereof wherein
X is O, S, or NH;
A is amino, diaminoalkyl, or heterocyclyl such as pyrrolidinyl optionally substituted with one or more, the same or different, $R^{15}$;
Z is N or CH;
$R^3$, $R^4$, $R^5$, $R^6$, $R^7$, $R^8$, $R^9$, $R^{13}$, and $R^{14}$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, $R^9$, $R^{13}$, and $R^{14}$ are optionally substituted with one or more, the same or different, $R^{15}$;

$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^7$ and $R^9$ are a halogen, one of or both.

In certain embodiments, $R^6$ and $R^8$ are a halogen, one of or both.

In certain embodiments, $R^4$ is a halogen, e.g., halogen is fluoro.

In certain embodiments, the disclosure relates to compounds of Formula IB:

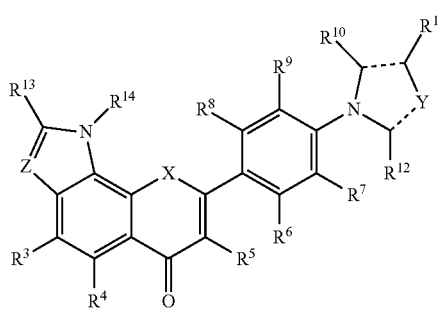

Formula IB or salt, prodrug, or ester thereof wherein
the dotted line is a double or single bond;
X is O, S, or NH;
Y is CH, CH$_2$, —CH$_2$CH$_2$—, O, S, N, or NH;
Z is N or CH;
$R^3$, $R^4$, $R^5$, $R^6$, $R^7$, $R^8$, $R^9$, $R^{10}$, $R^{11}$, $R^{12}$, $R^{13}$, and $R^{14}$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, $R^9$, $R^{10}$, $R^{11}$, $R^{12}$, $R^{13}$, and $R^{14}$ are optionally substituted with one or more, the same or different, $R^{15}$;

$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{13}$ is hydrogen, hydroxy, or alkyl.

In certain embodiments, $R^7$ and $R^9$ are a halogen, one of or both.

In certain embodiments, $R^6$ and $R^8$ are a halogen, one of or both.

In certain embodiments, $R^4$ is a halogen, e.g., halogen is fluoro.

In certain embodiments, the disclosure relates to a compound is selected from:
8-(4-(dimethylamino)phenyl)chromeno[7,8-d]imidazol-6(3H)-one,
8-(4-(pyrrolidin-1-yl)phenyl)chromeno[7,8-d]imidazol-6(3H)-one,
2-methyl-8-(4-(pyrrolidin-1-yl)phenyl)chromeno[7,8-d]imidazol-6(3H)-one, and
2-(4-(pyrrolidin-1-yl)phenyl)pyrano[3,2-g]indol-4(9H)-one.

In certain embodiments, the compound may optionally be substituted with one or more substituents.

In certain embodiments, the disclosure relates to compounds of Formula IC:

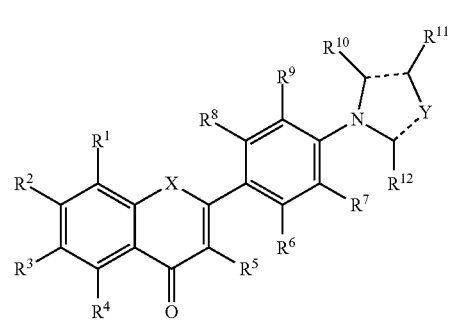

Formula IC or salt, prodrug, or ester thereof wherein
the dotted line is a single or double bond;
X is O, S, or NH;
Y is CH, CH$_2$, —CH$_2$CH$_2$—, O, S, N, or NH;
$R^1$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^1$ is optionally substituted with one or more, the same or different, $R^{15}$; or $R^1$ and $R^2$ and attached atoms form a 5 membered heterocylic ring optionally substituted with $R^{15}$;

$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;

$R^3$, $R^4$, $R^5$, $R^6$, $R^7$, $R^8$, $R^9$ $R^{10}$, $R^{11}$, and $R^{12}$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, $R^9$ $R^{10}$, $R^{11}$, and $R^{12}$ are optionally substituted with one or more, the same or different, $R^{15}$;

$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to compounds of Formula II:

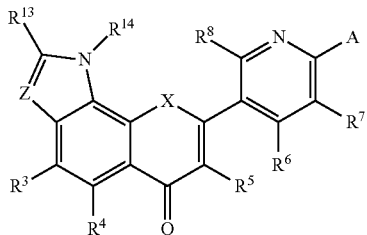

Formula II or salt, prodrug, or ester thereof wherein

X is O, S, or NH;

A is amino, diaminoalkyl, or heterocyclyl such as pyrrolidinyl optionally substituted with one or more, the same or different, $R^{15}$;

Z is N or CH;

$R^3$, $R^4$, $R^5$, $R^6$, $R^7$, $R^8$, $R^{13}$, and $R^{14}$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, $R^{13}$, and $R^{14}$ are optionally substituted with one or more, the same or different, $R^{15}$;

$R^{18}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^7$ is a halogen such as fluoro.

In certain embodiments, the compound is selected from:
8-(5-fluoro-6-(pyrrolidin-1-yl)pyridin-3-yl)chromeno[7,8-d]imidazole-2,6(1H,3H)-dione, and
8-(5-fluoro-6-(pyrrolidin-1-yl)pyridin-3-yl)-2-methyl-chromeno[7,8-d]imidazol-6(3H)-one or salts thereof.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more inhibitors can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the inhibitor(s) to carrier and/or other substances may vary from about 0.5 to about 100 wt % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit®

RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt % to 100 wt % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more inhibitors. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released.

Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compounds described herein can be administered in combination with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics.

Specific examples of compounds that can be adjunctively administered with the compounds include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

The additional active agent(s) can be formulated for immediate release, controlled release, or combinations thereof.

Methods of Use

In certain embodiments, the disclosure relates to methods of preventing or treating a BDNF and TrkB related disease or condition comprising the administering an effective amount of a pharmaceutical composition disclosed herein, to a subject in need thereof. In some embodiments, the subject is diagnosed with, exhibiting symptoms of, or at risk of the disease or condition. In some embodiments, the disease or condition is depression, anxiety, amytrophic later sclerosis, Alzheimer's disease, Huntington's disease, Rett syndrome, epilepsy, Parkinson's disease, dementia, diabetic neuropathy, peripheral neuropathy, obesity, or stroke.

In certain embodiments, the methods described herein include a method of treating or reducing the risk of disorders associated with activation of the TrkB receptor including neurological disorders, neuropsychiatric disorders, and metabolic disorders in a subject. Examples of neurological and neuropsychiatric disorders include depression, anxiety, Alzheimer's, CNS injuries, and the like. Examples of metabolic disorders include obesity and hyperphagia. This method includes the steps of selecting a subject with or at risk of developing the neurological disorder, neuropsychiatric disorder, or obesity, and administering to the subject a therapeutically effective amount of a compound disclosed herein. The compound can be administered systemically (e.g., orally, parenterally (e.g. intravenously), intramuscularly, intreperitoneally, transdermally (e.g., by a patch), extracorporeally, topically, by inhalation, subcutaneously or the like), by administration into the central nervous system (e.g., into the brain (intracerebrally or intra ventricularly), spinal cord, or into the cerebrospinal fluid), or any combination thereof.

The subject in need thereof can be a patient diagnosed as suffering from depression or anxiety. These diseases and their diagnoses are very clearly defined in the "Diagnostic and Statistical Manual of Mental Disorders (DSM-IV)" published by the American Psychiatric Association. This manual sets forth diagnostic criteria, descriptions and other information to guide the classification and diagnosis of mental disorders and is commonly used in the field of neuropsychiatry. In certain embodiments, the patient is being administered an antidepressant or anti-anxiolytic medication. In certain embodiments, the patient has been diagnosed by a mental health professional (e.g., a psychiatrist) with an anxiety or depression disorder. Anxiety can be a symptom of an underlying health issue such as chronic obstructive pulmonary disease (COPD), heart failure, or heart arrhythmia.

The subject in need thereof can be a patient diagnosed as suffering from being overweight or obese. Being overweight and obesity can be diagnosed by health or nutritional professionals (e.g., physicians, nurses, dieticians, and the like) when the patient's body mass index (BMI), a measurement which compares weight and height, is between 25 kg/m and 30 kg/m$^2$, and obese when it is greater than 30 kg/m$^2$.

Also provided is a method of promoting neuroprotection in a subject. This method includes the steps of selecting a subject in need of neuroprotection, and administering to the subject a therapeutically effective amount of a compound disclosed herein. A subject in need of neuroprotection can, for example, be a subject that has amyotrophic lateral sclerosis (ALS) or a central nervous system injury. A central nervous system injury includes, for example, a brain injury, a spinal cord injury, or a cerebrovascular event (e.g., a stroke). Methods can further comprise testing the effectiveness of a compound disclosed herein. Testing the effectiveness can include, but is not limited to, imaging (e.g., Magnetic Resonance Imaging (MRI)) and functional measurements (e.g., survival or clinical symptoms like analysis of speech patterns, logic, comprehension, memory, mood, and orientation).

Flavone Derivatives Possesses the Enhanced TrkB Stimulatory Activity

Figures 1, 2:
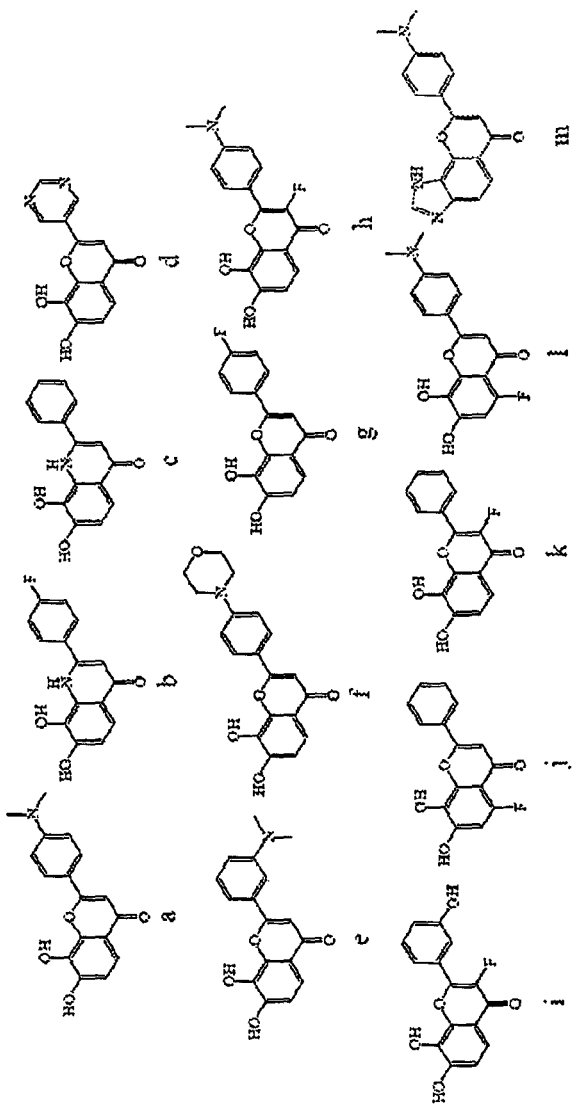
FIG. 2 shows data indicating 4'-dimethylamino-7,8-imidazole flavone exhibits elevated TrkB stimulatory activity. A, The chemical structures of various synthetic flavonoids. B, 4'-dimethylamino-7,8-imidazole flavone displays stronger TrkB stimulatory activity than compound a. Primary cortical cultures from E17 rat embryos were treated with 500 nM of various synthetic flavone derivatives for 15 min. The cell lysates (20 μg) were analyzed by the immunoblotting (upper panels). The cell lysates (20 μg) were analyzed with p-Akt ELISA (lower panel) (*, P<0.05; , P<0.01; *, P<0.001 vs control; one-way ANOVA). The data were from two sets of replicated experiments (mean±SEM). C, 4'-dimethylamino-7,8-imidazole flavone strongly activates TrkB receptor in mouse brain. One mg/kg of various indicated compounds were orally administrated into C57 BL/6J mice and TrkB phosphorylation and its downstream signaling cascades including Akt and MAPK in the hippocampus of mouse brain were analyzed by immunoblotting at 4 h. Both compound a and m displayed the strongest TrkB stimulatory effect (top panel). The downstream p-Akt and p-MAPK activity coupled to the TrkB activation patterns ($3^{rd}$ and $5^{th}$ panels). P-Akt 473 ELISA in drug treated mouse brain was analyzed (bottom panel) (***, P<0.001 vs control; one-way ANOVA). The data were from two sets of replicated experiments (mean±SEM).
Figure 2:
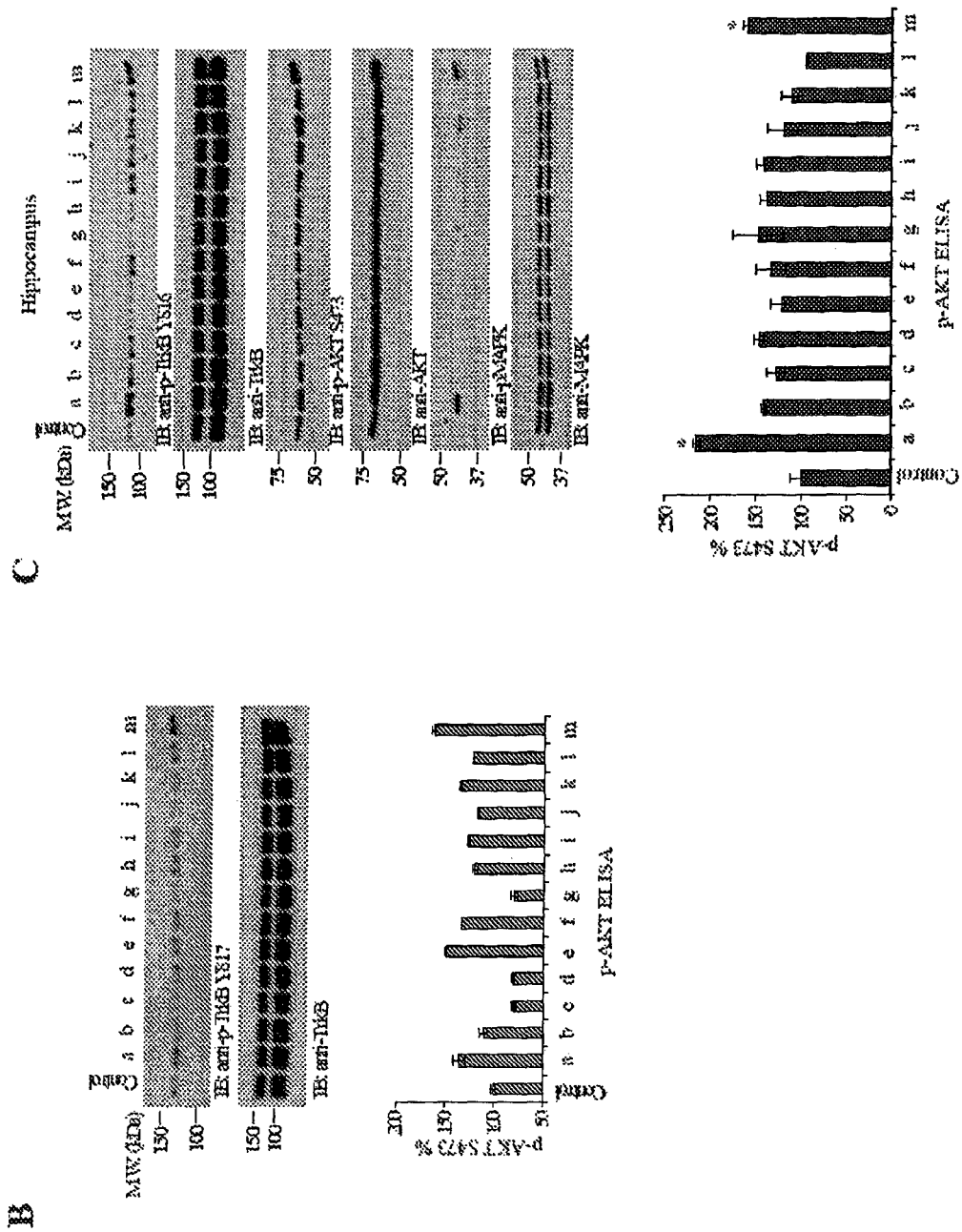
Figures 1, 3:
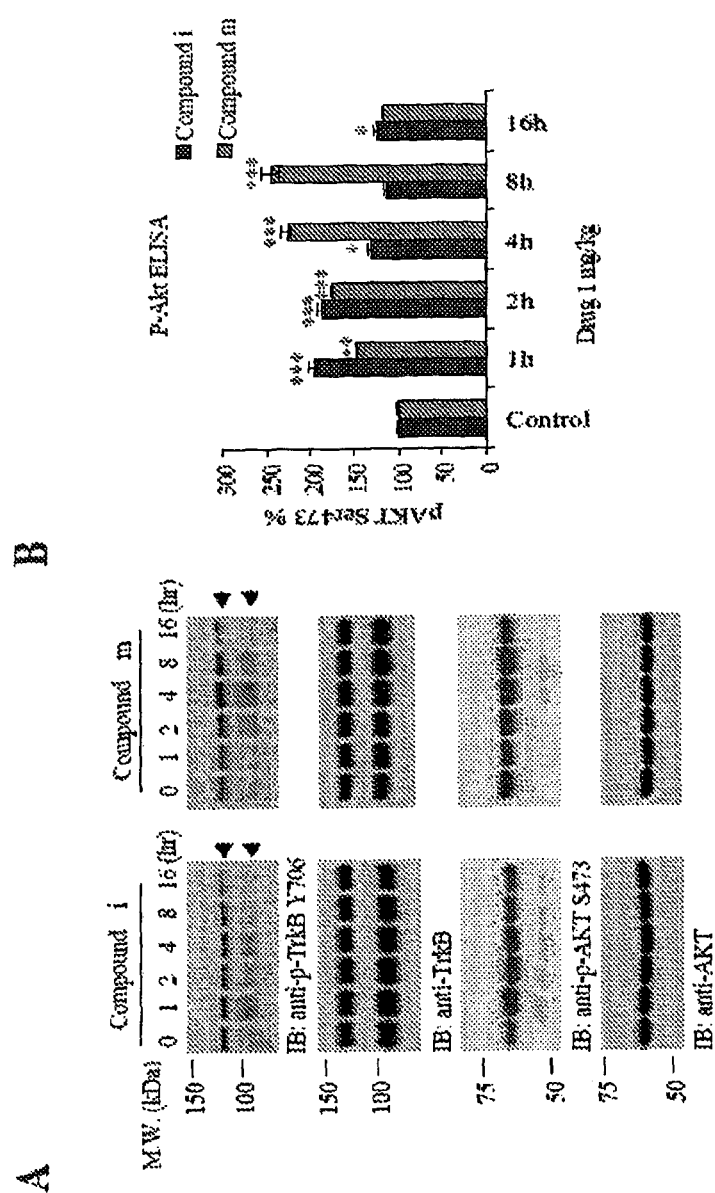
FIG. 3 shows data indicating 4'-dimethylamino-7,8-imidazole flavone strongly activates TrkB and reduces the immobility in forced swim test. A, Time course assay with 4'-dimethylamino-7,8-imidazole flavone. One mg/kg of compound (i) and compound (m) were orally administrated into C57 BL/6J mice and TrkB phosphorylation and its downstream signaling cascades including Akt in mouse brain were analyzed by immunoblotting at various time points. TrkB activation by compound m peaked at 4 h, whereas the maximal TrkB activation by compound i in mouse brain occurred at 1-2 h. Arrows indicate the p-TrkB in mature glycosylated or unglycosylated forms (top panels). The downstream Akt activation pattern tightly correlated with the upstream TrkB activation ($3^{rd}$ panels). B, P-Akt 473 ELISA in drug-treated mouse brain was analyzed with 20 μg of brain lysates. (*, P<0.001 vs control; one-way ANOVA). The data were from two sets of replicated experiments (mean±SEM). C, Forced swim test with compound m and i. Male C57BL/6J mice (6 mice/group) were orally administrated by gavage with 5 mg/kg compound (m) or compound (i) and vehicle solvent saline for 21 days and subjected to a forced swim test (6 min, immobility recorded in the last 4 min). Data are presented as mean±SEM. (n=6, *P<0.0001 vs vehicle, Student t-test). D. Locomotor activity assay. The above drug-treated mice were subjected locomotor activity at day 22. Compound m but not i significantly increased the locomotor activity compared to vehicle control. Data are presented as mean±SEM. Analysis of variance (ANOVA) revealed significant difference between vehicle and either compound m or i (n=6.
Figures 2, 3:
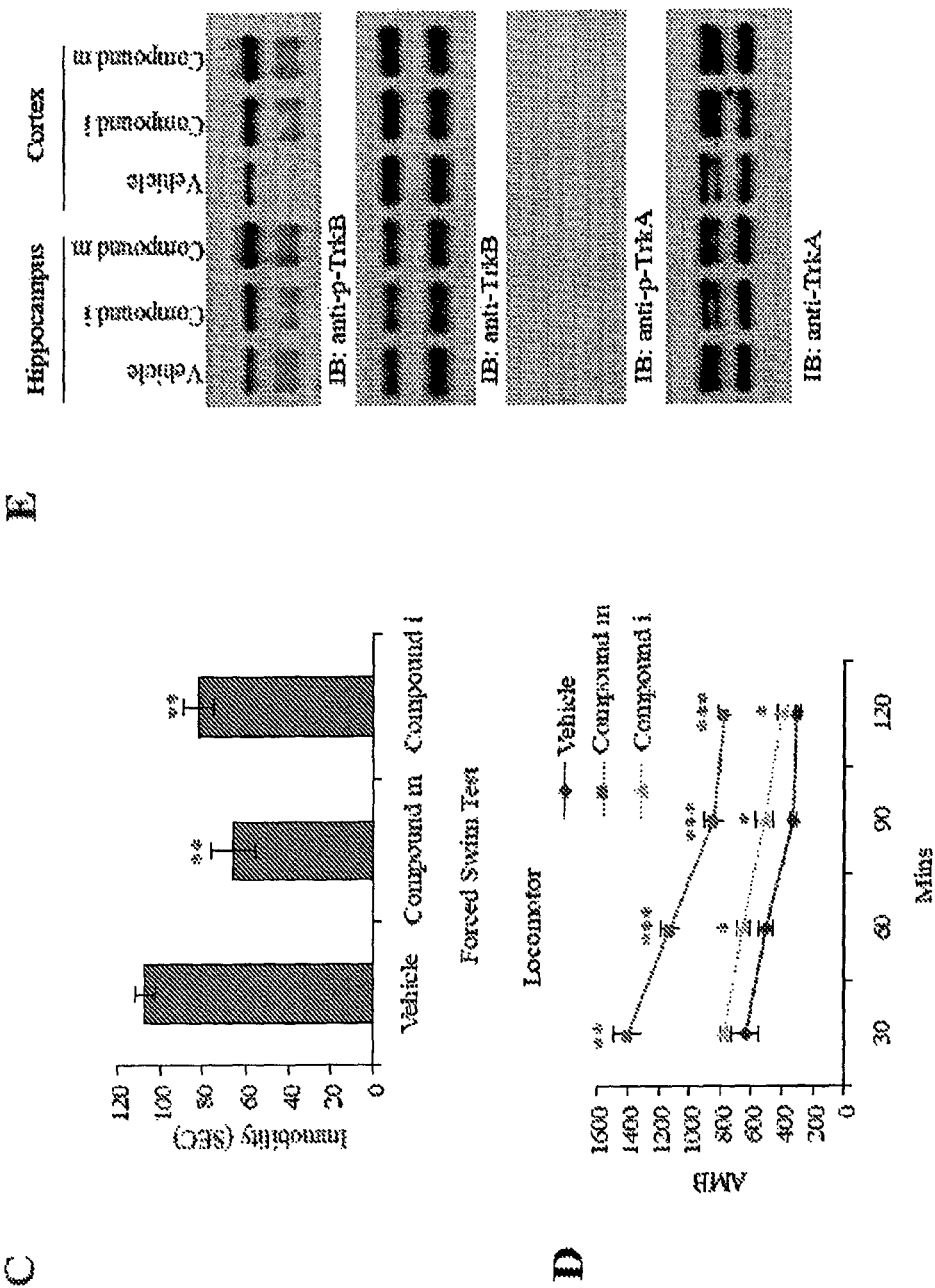

Certain flavone derivatives possess favorable in vitro ADMET features and are active in mouse models of depression. For example, in the mouse brain hippocampus, 4'-pyrrolidino-7,8-methylimidazole-flavone (also referred to as 2-methyl-8-(4-(pyrrolidin-1-yl)phenyl)chromeno[7,8-d] imidazol-6(1H)-one) activates the TrkB receptor and exerts robust antidepressant effects in both FST and TST assays. Studies suggest that for 7,8-dihdyroxyflavone (7,8-DHF) the 7,8-dihydroxy groups on the A ring and the middle heteroatomic Chromen-4-one C ring are important for the TrkB stimulatory effect. Additionally, the 4'-position on the B ring is also important for the agonistic effect. An electron-withdrawing group, such as F, or an electron-donating OH at this position suppresses the activity. Replacement with a dimethylamino- or pyrrolidino-group yields the desired activity. Based on 4'-dimethylamino-7,8-DHF, a series of compounds were synthesized. Fluoride groups were added at different positions, and in certain compounds the 7,8-dihydroxy groups were replaced with an imidazole ring or the dimethylamino group was changed to a pyrrolidino ring. Compounds h and i indicate that addition of a fluoride group does not substantially affect TrkB stimulatory activity (FIG. 2). Replacing the 7,8-dihydroxy groups with an imidazole ring in compound m elevated its agonistic activity compared to compound a, though the in vivo TrkB stimulatory activity remained comparable for the two compounds (FIGS. 2B & C). Although compound m strongly activated TrkB in mouse brain and decreased the immobility in FST, this compound highly augmented the locomotor activity as well (FIG. 3), indicating that it might reduce the immobility in FST by increasing the locomotor activity.

Because the dimethylamino group may be prone to be metabolic demethylation, the dimethylamino group was replaced with a pyrrolidino group. Compound o displayed higher agonistic activity than compound m, and it also attenuated the locomotor enhancement effect displayed by compound m (FIG. 5). Compound o was active in both FST and TST depression behavioral assays.

Catechol-related compounds sometimes possess poor pharmacokinetic profiles due to oxidation, glucuronidation, sulfation or methylation. For instance, catechol-containing Apomorphine, is a non-narcotic morphine derivative that acts as a potent dopaminergic agonist. Apomorphine metabolism occurs through several enzymatic pathways, including N-demethylation, sulfation, glucuronidation, and catechol-O-methylation as well as nonenzymatic oxidation. L-DOPA is the primary component of Parkinson's disease (PD) therapy; this drug is usually administered orally, but it is extensively metabolized in the gastrointestinal tract, so relatively little circulates in the bloodstream as intact L-DOPA. To minimize the conversion to dopamine outside the central nervous system, L-DOPA is usually given in combination with peripheral inhibitors of Aromatic L-Amino Acid Decarboxylase and COMT (catechol methyltransferase) inhibitor.

In vivo metabolism studies shows that 7,8-DHF is subjected to oxidation, glucuronidation, sulfation and methylation. Among the modifications, glucuronidation and sulfation are thought to be responsible for the in vivo metabolism of the flavonoids. In addition, the O-methylated metabolites were detected in both the plasma and brain samples after oral administration. These modification pathways may explain the relatively short half-life of 7,8-DHF. Alteration of this labile group into the bioisosteric imidazole derivative escalates the PK profiles in compound o (Table 5).

In vitro ADMET profiles have been examined for compounds disclosed herein. Compound n, o and p exhibited negligible cytotoxicity or genotoxicity (FIG. 6). The hERG inhibition index is suboptimal for compound o. The microsomal stability and reactive metabolic screening assays support that compound o is more stable than compound p in vitro. The in vivo half-life of compound o is about 103 min in mice and its oral bioavailability is 2%. Compound o exhibited improved in vivo PK profile than compound a (Table 5). Studies herein indicate that 7,8-imidazole and 4'-pyrrolidone-substituted flavones are promising drug candidates.

EXPERIMENTAL

Cells, Reagents, and Mice

Anti-p-TrkB 817 was from Epitomics. Anti-p-TrkB 706 was from Santa Cruz. Anti-TrkB antibody was from Cell signaling. The wild-type C57BL/6 mice were bred in a pathogen-free environment in accordance with Emory Medical School guidelines. All chemicals not included above were purchased from Sigma. 7,8-DHF was purchased from TCI. The fluoro-substituted flavonoids were from Sundia (Shanghai, China). Compound e and f were provided by NIMH, Chemical Synthesis and Drug Supply Program at RTI. NMR spectrum (Bruker AV300K, 300 MHz), MS spectrum (Shimadzu LCMS), HPLC (PE, dual pumper, SPD detector, ODS-C18 reverse phase, 254 nm, $CH_3CN$—$H2O$— 0.1% TFA). Phospho-TrkB Y816 antibody was described before. This phospho-TrkB was utilized for immunostaining the brain sections. Anti-TrkB (Cell Signaling, which recognizes both full-length and truncated TrkB) was used for immunoblotting. P-Akt 473 Sandwich ELISA was from Cell Signaling. BDNF was from Peprotech. Anti-phospho-TrkA 794, anti-TrkA, Phospho-Akt-473, anti-Akt, and Antiphospho-Erk1/2 antibodies were from Cell Signaling.

Synthesis of Imidazole-Flavonoid and Indole-Flavonoid Derivatives

Figure 1:
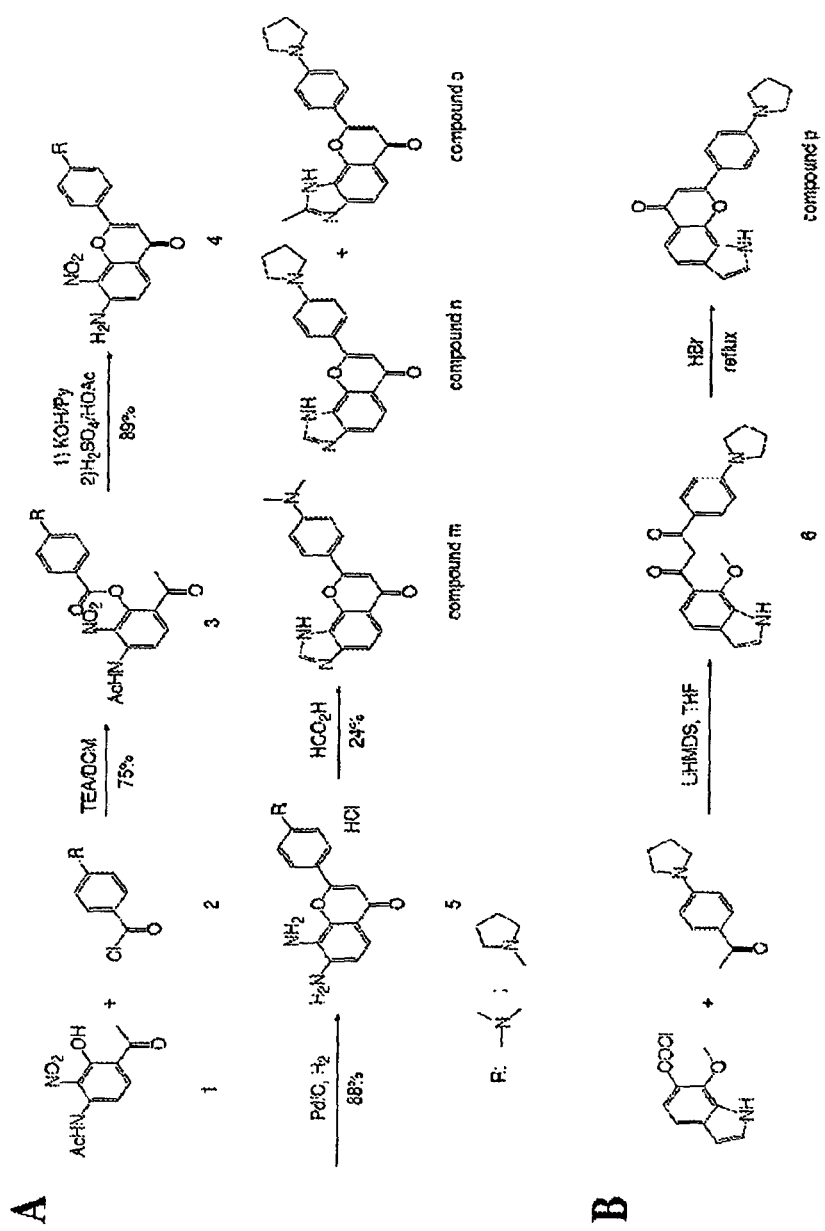
FIG. 1 illustrates the synthesis of various embodiments. A, Schematic diagram of synthetic routes for 4'-dimethylamino-7,8-imidazole flavone (compound m, n and o). R represents dimethylamino group or N-pyrrolidino-group. B, Schematic diagram of synthetic route for compound p.

The catechol or phenyl group plays an important role in regulating the TrkB agonistic effects of 7,8-dihdyroxyflavone (7,8-DHF). Flavone derivatives were synthesized. In FIG. 1A, 4-(dimethylamino)benzoyl chloride (2) was coupled to N-(4-acetyl-3-hydroxy-2-nitrophenyl)acetamide (1) in the presence of triethylamine at 0° C. to yield 3-acetamido-6-acetyl-2-nitrophenyl 4-(dimethylamino)benzoate (3), which was subsequently cyclized. The yellow solid was collected and dissolved in acetic acid and concentrated sulfuric acid to afford 7-amino-2-(4-(dimethylamino)phenyl)-8-nitro-4H-chromen-4-one (4). This compound was reduced to generate 7,8-diamino-2-(4-(dimethylamino)phenyl)-4H-chromen-4-one hydrochloride (5). A solution of this compound was refluxed in $HCO_2H$ for 1 h to produce a yellow solid, which was recrystallized to yield 8-(4-(dimethylamino)phenyl)chromeno[7,8-d]imidazol-6(1H)-one (compound m). The 4'-pyrrolidino imidazole derivatives were synthesized with similar routes, producing a mixture of imidazole-flavonoid (compound n) and methyl-imidazole-flavonoid (compound o) with 60:40 ratio (FIG. 1A), which were purified with pre-HPLC to give compound n as an orange solid and a dark-yellow solid compound o. To a solution of compound 4'-pyrrolidino-phenylmethylketone, in dry THF at −20° C., LiHMDS was added and the mixture was stirred at −20° C. for 1 h, then 7-methoxy-6-indolecarboxylic chloride was added, and the mixture was stirred for another 1 h, then stirred at room temperature overnight. The mixture was quenched with $NH_4Cl$ water solution and extracted with ethyl acetate to give compound 6 (1-(4'-pyrrolidino-phenyl)-3-(7'-methoxy-6-indolyl)propane-1,3-dione), which was subsequently cyclized in the presence of HBr to yield compound p (FIG. 1B).

Preparation of Compound (m)

Preparation of 3-acetamido-6-acetyl-2-nitrophenyl 4-(dimethylamino)benzoate (3)

To a mixture of N-(4-acetyl-3-hydroxy-2-nitrophenyl)acetamide (1, 1 g, 4.1 mmol, 1.0 eq) and triethylamine (1.5 mL) was added 4-(dimethylamino)benzoyl chloride (2, hydrochloride, 6.3 mmol, 1.5 eq.) in 3 portions at 0° C. Then the mixture was stirred at rt for 3 h. Diluted with DCM (100 mL), washed with 1N HCl (100 mL) and water (50 mL). The organic phase was separated, dried with sodium sulfate, filtered and concentrated to afford gray solid, which was purified by SGC (PE/EA=1/1) to afford (3, 1.2 g, yield: 75%).

Preparation of 7-amino-2-(4-(dimethylamino)phenyl)-8-nitro-4H-chromen-4-one (4)

A mixture of 3-acetamido-6-acetyl-2-nitrophenyl 4-(dimethylamino)benzoate (3, 2 g, 1.0 eq.) and potassium hydroxide (8 g, 2.0 eq.) in pyridine (20 mL) was heated to 60° C. for 1 h and poured into icy 1N HCl (100 mL). The yellow solid was collected and dissolved in acetic acid (20 mL) and concentrated sulfuric acid. The resulting mixture was heated to 110° C. for 30 min. The mixture was cooled to rt and poured into saturated sodium carbonate. The yellow solid was filtered and dried in vacuo to afford 7-amino-2-(4-(dimethylamino)phenyl)-8-nitro-4H-chromen-4-one (4) (1.5 g, yield: 89%)

Preparation of 7,8-diamino-2-(4-(dimethylamino)phenyl)-4H-chromen-4-one hydrochloride (5)

A solution of 7-amino-2-(4-(dimethylamino)phenyl)-8-nitro-4H-chromen-4-one (4, 900 mg, 2.77 mmol) and 10% Pd/C (450 mg) in methanol (9 mL) and concentrated hydrochloride (aq., 9 mL) was stirred at the atmosphere of hydrogen overnight. The solid was filtered and the filtrate was evaporated at reduced pressure to afford 7,8-diamino-2-(4-(dimethylamino)phenyl)-4H-chromen-4-one hydrochloride (5) as a light yellow solid (810 mg, yield: 88%).

Preparation of 8-(4'-(dimethylamino)phenyl)chromeno[7,8-d]imidazol-6(1H)-one (m)

A solution of 7,8-diamino-2-(4-(dimethylamino)phenyl)-4H-chromen-4-one hydrochloride (500 mg) in $HCO_2H$ (5 mL) was heated to reflux for 1 h. The volatiles were evaporated in reduced pressure and the residue partitioned between EA/isopropanol=20/1 (50 mL) and saturated sodium carbonate (25 mL). The organic phase was separated, dried with sodium sulfate, filtered and concentrated to afford yellow solid, which was recrystallized from EA (25 mL) to afford light yellow solid (111 mg, yield: 24%). $^1$H NMR (300 MHz, DMSO-d$^6$) δ 8.46 (m, 1H), 10.09 (br s, 1H), 8.01 (m, 2H), 7.82 (m, 1H), 7.61 (m, 2H), 6.84~6.88 (m, 3H), MS-ESI: calculated: 305. found: 306(M+H)$^+$. HPLC: 99.23%.

Preparation of 8-(4'-(pyrrolidino-)phenyl)chromeno [7,8-d]imidazol-6(1H)-one (Compound n and Methylated Compound o)

To a solution of compound N-(4-acetyl-3-hydroxy-2-nitrophenyl) acetamide (1, 700 mg, 2.94 mmol) in dry DCM (dichloromethane, 10 mL) was added DIPEA (N,N-Diisopropylethylamine, 0.8 mL) and followed by compound 4'-N-pyrrolidino-benzoyl chloride (950 mg) at 0° C. and the resulting mixture was stirred at room temperature overnight. The mixture was quenched with water and extracted with DCM, the combined extracts were washed with water and brine, dried over Na$_2$SO$_4$. Concentrated and purified by silica gel (PE~PE:EA=10:1~7:1~5:1~3:1) to give the coupled ester compound as an orange solid (750 mg), which was then followed the similar procedures as described for compound m. After cyclization with KOH/pyridine, followed by H$_2$SO$_4$/AcOH reflux, the nitro group in intermediate was reduced with Fe (300 mg, 5.36 mmol) and NH$_4$Cl (154 mg, 2.85 mmol) to yield the reduced 7,8-diamino-compound. A mixture of compound 7,8-diamino-2-(4'-(N-pyrrolidino-)phenyl)-4H-chromen-4-one hydrochloride (1.1 g) in HCOOH (10 mL) was refluxed for 2 h. TLC showed the reaction was over. Combined with other batches, the mixture was basified to pH~8 by 1 N NaOH, the mixture was then concentrated and purified by silica gel (DCM~DCM: MeOH=100:1~50:1~20:1) to give a mixture of compound n and methylated compound o (80 mg), which was purified by pre-HPLC to give compound n as orange solid (50 mg, confirmed by 1H-NMR); $^1$HNMR (400 MHz, CD3OD): δ 8.81 (s, 1H), 8.04 (m, 3H), 7.68 (d, J=8.8 Hz, 1H), 6.78 (s, 1H), 6.66 (d, J=8.8 Hz, 2H), 3.37 (m, 4H), 2.07 (m, 4H); HPLC: 96%; MS-ESI: calculated 331.4. found 332.1 (M+1)$^+$, and compound o as dark-orange solid (25 mg, confirmed by 1HNMR). $^1$HNMR (400 MHz, CD3OD): δ 8.09 (d, J=8.4 Hz, 1H), 8.01 (d, J=8.4 Hz, 1H), 6.78 (s, 1H), 6.69 (d, J=8.8 Hz, 2H), 3.41 (m, 4H), 2.92 (s, 3H), 2.10 (m, 4H); HPLC: 94%; MS-ESI: calculated: 345.4. found: 345.9 (M+1)$^+$.

Preparation of Compound p

To a solution of compound 4'-N-pyrrolidino-benzoyl methyl ketone (154 mg, 0.813 mmol) in dry THF (10 mL) at −20° C. was added LiHMDS (2 mL, 2 mmol) and the mixture was stirred at −20° C. for 1 h. Compound 7-methoxy-6-indoloyl chloride (200 mg, 0.976 mmol) with (COCl)$_2$ in dry THF was added and the mixture was stirred at −20° C. for 1 h then room temperature overnight. TLC and LC-MS showed the desired product was found. The mixture was quenched with NH$_4$Cl aqueous and extracted with ethyl acetate (EA), the combined extracts were washed with water and brine, dried over Na$_2$SO$_4$. Concentrated and purified by silica gel (PE~PE:EA=5:1~2:1) to give intermediate compound 6, which was refluxed in HBr (48%, 6 mL) for 3 h. TLC showed the reaction was over. Combined with other batches and cooled to rt., water was added and the mixture was basified to pH~8 by NaOH (1 N) and concentrated and purified by silica gel (DCM~DCM:MeOH=20:1~10:1) to give crude compound p as a brown solid. This crude product was purified by pre-HPLC to give compound p as a brown solid. $^1$HNMR (400 MHz, DMSO-d$^6$): δ12.40 (br s, 1H), 8.16 (d, J=8.8 Hz, 2H), 7.70 (s, 1H), 7.57 (s, 2H), 6.80 (s, 1H), 6.68 (m, 3H), 3.36 (m, 4H), 2.00 (m, 4H); HPLC: 99%; MS-ESI: calculated: 330.4. found: 331.1 (M+1)$^+$.

4'-Dimethylamino-7,8-imidazole-flavone Displays Increased TrkB Stimulatory Effect The electron donor dimethylamino group on 4' position of B ring significantly elevates the agonist effect. Replacing the 3'-dimethylamino group or 4'-morpholino group was tested for TrkB agonistic activity. To compare the TrkB activation by these compounds, primary cortical cultures were prepared and treated them with 500 nM of various compounds for 15 min and collected the cell lysates. Immunoblotting revealed that compound m exhibited stronger effect in triggering TrkB activation than compound 4'-DMA-7,8-DHF (compound a). 3'-dimethylamino-7,8-DHF and 4'-morpholino-7,8-DHF exhibited comparable activity as compound a. Fluoride substitution at position 3 or 5 did not significantly affect TrkB agonistic activity. Fluoride substitution at the 4' position on B ring inhibited its activity, which might be due to its electron-withdrawing effect. Replacing an O atom with an N atom in the C ring diminished agonistic activity (FIG. 2B, upper panel). The p-Akt ELISA analysis results were similar to the TrkB activation pattern (FIG. 2B, lower panel).

Each compound (1 mg/kg) was orally administrated and TrkB activity was monitored at 4 h. Compound a activated the TrkB receptor; 4'-dimethylamino-7,8-imidazole-flavone (compound m) also robustly activated TrkB. The rest of compounds displayed a similar effect as was observed by the in vitro assay (FIG. 2C, top panel). Accordingly, the downstream p-Akt and p-MAPK signalings were strongly activated by both compound a and m. p-Akt ELISA analysis also correlated with the observations of p-TrkB immunoblotting (FIG. 2C, bottom panel).

4'-Dimethylamino-7,8-imidazole-flavone is Active in Mouse Models of Depression with Increased Locomoter Activity 4'-dimethylamino-7,8-imidazole-flavone (compound m), was administered to C57BL6 mice at 1 mg/kg via oral gavage. Compound i was employed in the same procedure. The mouse brains were collected and TrkB activation and its downstream Akt signaling were analyzed by immunoblotting. Compound m activated TrkB receptor in a time-dependent manner peaking at 4 h and then fading away at 16 h. The p-Akt signal was in alignment with the upstream p-TrkB activity. Compound i displayed less effect on TrkB activation than compound m (FIG. 3A, top and 3$^{rd}$ panels). P-Akt ELISA analysis tightly correlated with p-Akt immunoblotting results for both compounds. Compound m activated Akt gradually and climaxed at 8 h where the p-Akt signal was elevated by about 250% compared to the control. Compound i also elicited p-Akt activation peaking at 1 h, declining at 4 h and returning to baseline at 8 h. The peak magnitude of Akt activation by compound i was significantly less than compound m (FIG. 3B).

Forced swim test (FST) is broadly used for screening potential antidepressant drugs and is widely used to measure antidepressant activity. To explore whether these compounds possess an antidepressant effect, C57/BL6 J mice were chronically treated with 5 mg/kg of the compound, once a day for 3 weeks. At the end of the treatment, the locomoter activity assay was conducted, followed by a forced swim test. Both compounds significantly reduced the immobility. The effect of compound m was more robust than that of compound i (FIG. 3C). Nonetheless, Compound m substantially augmented locomoter activity compared to compound i and vehicle control (FIG. 3D). Immunoblotting with brain tissues from both cortex and hippocampus demonstrated that both compounds m and i escalated TrkB phosphorylation after 3 weeks of drug treatment compared to vehicle control, but compound m displayed a stronger effect than compound i. The TrkA receptor was not activated by any of these compounds (FIG. 3E), demonstrating that they are TrkB receptor-specific agonists.

4'-Pyrrolidino-7,8-methyl-imidazole-flavone Demonstrates Greater Potency than 4'-Dimethylamino-7,8-imidazole-flavone Though compound m possesses robust TrkB stimulatory effect and reduces immobility in forced swim test, it escalates locomotor activity after 3 weeks of administration. Several imidazole or indole-substituted flavonoid compounds were synthesized (FIG. 4A). Immunoblotting and p-Akt ELISA analysis demonstrated that both compounds o and p display higher activity than compound m in triggering TrkB and Akt activation in primary neurons (FIG. 4B). We made similar observations about TrkB receptor and Akt activation by these compounds in mouse brain after 2 h oral administration of a 1 mg/kg dosage (FIG. 4C). Antidepressant effects of compound o and p were tested in both forced swim test and tail suspension test assays.

4'-Pyrrolidino-7,8-methyl-imidazole-flavone Demonstrates Antidepressant-Like Profile without Altering Locomoter Activity Mice were treated with compounds o and p at dosage of 2.5 mg/kg via oral gavage once a day for 3 weeks. FST showed that compound o significantly reduced the immobility by 45% compared to vehicle control (FIG. 5A). The tail suspension test (TST) has become one of the most widely used models for assessing antidepressant-like activity in mice. The test is based on the fact that animals subjected to the short-term, inescapable stress of being suspended by their tail, will develop an immobile posture. Various antidepressant medications reverse the immobility and promote an escape-related behavior. Compound o significantly reduced the immobility versus vehicle control (FIG. 5B). Further, locomotor activity analysis revealed that neither compound o nor p altered the motion activity compared to vehicle control (FIG. 5C). Immunoblotting analysis with brain tissues demonstrated that both compounds o and p markedly activated TrkB receptor, which was observed using both anti-p-TrkB Y816 and anti-p-TrkB Y706 antibodies. P-Akt immunoblotting also correlated with the upstream TrkB activation (FIG. 5D, top, $2^{nd}$ and $4^{th}$ panels). Quantitative p-Akt ELISA assay supported that both compounds notably activated Akt, fitting with the observations by Western blotting (FIG. 5D, bottom panel). Immunohistochemistry staining with anti-p-TrkB demonstrated that TrkB receptor was activated by these two chemicals in dentate gyrus after 3 weeks of treatment (FIG. 5E, white arrows). Chronic treatment with 4'-pyrrolidino-7,8-methyl-imidazole-flavone promotes TrkB activation in the hippocampus of mice and exhibits potent antidepressant-like profile.

In Vitro ADMET Profiles of the Imidazole Derivatives 7,8-DHF and other flavonoids have been reported to possess anti-genotoxic effects against DNA lesions and micronuclei induced in human hepatocellular carcinoma cells, HepG2, by a potent mutagen and carcinogen benzo[a]pyrene (B(a)P). In vitro and in vivo ADMET (ADME plus toxicity) of certain compounds were examined. An LDH cytotoxicity assay, using HepG2 cells treated with various compounds for 24 h, demonstrated that none of the tested compounds induced noticeable cytotoxicity even up to 100 μM, suggesting that these compounds do not trigger cell death even at very high concentrations (FIG. 6A). Micronuclei formation is an important endpoint in genotoxicity study. To assess whether these synthetic compounds possess any potential carcinogenicity, the micronucleus assay was conducted by treating HepG2 cells with 50 μM of various compounds for 24 h, followed by DAPI staining. Quantitative analysis revealed that none of the tested compounds exhibited significant effect, whereas the positive control B(a)P robustly induced micronuclei (FIG. 6B). Next, a Comet assay was performed with 100 μM drug-treated HepG2 cells. As a positive control, etoposide, a topoisomerase inhibitor, which causes DNA strand breaks was used. Interestingly, compound m but not other synthetic derivatives induced DNA lesions (FIG. 6C). Hence, these toxicity experiments support that compounds n, o and p possess negligible cytotoxicity or genotoxicity.

To explore these compounds' in vitro ADMET profiles, we conducted numerous in vitro assays. Human liver microsomal stability assay showed that after 1 h incubation, compound p had 1.2% remaining, whereas compound o had 25.4% unchanged, supporting that compound o is more metabolically stable than compound p. Reactive metabolic screening assays support that compound o is quite stable in vitro, whereas compound p formed numerous adducts, indicating that it is labile and reactive to numerous biochemicals or proteins in liver microsomal lysates.

CYP screen inhibition demonstrated that at 3 μM, CYP1A2 was inhibited about 27.3% by compound o, whereas 37.4% was blocked by compound p. At 30 μM, the inhibition patterns contained similar trends. To test the possible cardiovascular toxicity, hERG inhibition triggered by compound o was examined. The hERG inhibition assay revealed that compound o did not possess any concentration-dependent inhibition activity of hERG. A human plasma protein binding experiment showed that both compounds o and p displayed approximately 99.9% of protein binding. Hence, compound o possesses a more preferable in vitro ADMET profile than compound p, fitting with its promising in vivo antidepressant efficacy.

To investigate whether compound o possesses an improved in vivo PK profiles compared to compound a, in vivo pharmacokinetic studies in mice was conducted. For compound a, the standard dosage of 1 mg/kg via i.v. injection and 5 mg/kg for P.O. route was employed. At 1 mg/kg, the in vivo half-life, $t_{1/2}$, of compound a in circulation is around 9 min and AUC last is about 5930 (min*ng/ml), but the bioavailability of compound a is not measurable at 5 mg/kg. Presumably, the dosage is too low for the in vivo PK assay. Thus, the doses of the tested compound o were increased. The $t_{1/2}$ for compound o is about 103 min with AUC last approximately 18746 (min*ng/ml) at a dose of 3 mg/kg. Moreover, the bioavailability is around 2% for compound o at a 10 mg/kg dosage.

Phospho-AktS473 ELISA

PathScan Phospho-Akt1 (Ser473) Sandwich ELISA kit was purchased from Cell Signaling (Cat. #7160). 100 μl sample in sample diluent (supplied in the kit) was added to each well and incubated overnight at 4° C. After 4× wash with 200 ul wash buffer (supplied in the kit), 100 ul/well detection antibody was added and incubated for 1 hour at 37° C. After 4× wash, 100 μl of HRP-linked secondary antibody (supplied in the kit) was added and incubated for 30 minutes at 37° C. After a final wash, 100 μl of TMB substrate was added to each well and incubated for 10 minutes at 37° C. The reaction was stopped by adding 100 μl/well stop solution. Record the values of each well using microplate reader at 450 nm and 650 nm. The optical density was determined by the subtraction of the reading at 650 nm from the reading s at 450 nm.

TrkB Agonists Drug Administration

Male C57BL/6 mice aged of two months were administrated orally with 4'-DMA-7,8-DHF derivatives at a single dose of 1 mg/kg for 4 h. The control mice were injected with saline. The mice were sacrificed and brains were homogenated and ultracentrafuged. The supernatant (40 μg) was employed for SDS-PAGE and immunoblotting analysis with indicated antibodies, respectively. Male C57BL/6 mice aged of two months were administrated orally with compound (i) or (m) at the dose of 5 mg/kg/day each and compound o or p at the dose of 2.5 mg/kg/day each for 21 days. BrdU (100 mg/kg) was i. p. injected two hours before the TrkB agonist treated animals were sacrificed and the hippocampal section lysates were analyzed by immunoblotting with p-TrkB and total TrkB antibodies, p-AKT ELISA.

Immunohistochemistry Staining

Brain tissues were fixed in 4% paraformaldehyde overnight followed by paraffin embedding. Sections of 6 μm were cut. For immunohistochemical staining, brain sections were deparaffinized in xylene and rehydratedm in graded alcohols. Endogenous peroxidase activity was blocked by 3% hydrogen peroxide for 5 min and all slides were boiled in 10 mM sodium citrate buffer (pH 6.0) for 10 min. Phosphorylated TrkB 816 and TrkB were detected using specific antibodies. Paraffin section were deparaffinized in xylene and rehydrated gradient ethanol solution. Samples were boiled in 10 mM sodium citrate buffer for 20 min for antigen retrieval purpose. Brain sections were incubated with anti-TrkB (BD Biosciences, San Jose, Calif.) 1:50, p-TrkB 1:300 dilution. Secondary antibody was applied using anti-rabbit-Alexa 594 (red), anti-mouse-fluorescein isothiocyanate (FITC) (green). DAPI (blue) was used for nuclear staining.

Force Swim Test

Adult male mice (2-3 months old) were randomly submitted to a forced swim test without a preswim. Test compounds were orally administrated by gavage for 21 days. The mice were allowed to adapt to the test room for 2 days. The mice were placed in a clear glass cylinder with a diameter of 16 cm, half-filled with clear water at 24° C. (water depth of 14 cm did not allow the mice to reach the bottom of the cylinder) for a total of 6 min, and immobility was recorded during the last 4 min by an investigator blind to the treatment.

Tail Suspension Test

One suspends mice by the tail to a horizontal ring stand bar 30 cm above the floor using adhesive tape for 6 minutes and videotaped. Latency to immobility and time spent immobile will be scored for each mouse. Following the test, mice will be returned to their home cage. Immobility scores were compared by unpaired t test.

Locomotor Activity

Locomotor activity was assessed using an automated system (San Diego Instruments, La Jolla, Calif., USA) with photobeams that recorded ambulations (consecutive beam breaks). Drug-treated mice were placed in the locomotor chambers, and their activity was recorded for 2 h with 30 min interval.

Neurogenesis Analysis in TrkB Agonists-Treated Hippocampus

Adult male mice (2-3 months old) were orally administrated with saline, compound o, and p (2.5 mg/kg) for 21 days. Then BrdU (100 mg/kg) was i.p. injected. In 2 h, the mice were perfused with 4% paraformaldehyde. Immunohistochemical staining was performed on formalin-fixed paraffin embedded sections. Sections from brain were cut, deparaffinized in xylene, and rehydrated in graded alcohols. The slides were boiled in 10 mM citric acid (pH 6.0) for 10 min, followed by an incubation in 2 N HCl for 10 min in room temperature. The slides were then permeabilized and blocked with 1% BSA in 0.2% PBS Tween-20 (PBST). The incorporated BrdU were stained using anti-BrdU-FITC (Abcam, USA) at 4° C. for 16 h. After three times of washing in PBS, the cells were then stained with DAPI for another 10 min at room temperature. The slides were finally mounted with AquaMount (Lerner Laboratories, USA) containing 0.01% 1,4-diazobicyclo(2,2,2)octane and examined under a fluorescence microscope.

Micronucleus Assay

The cells treated with 7,8-DHF derivatives at 50 μM for 24 hrs were washed with PBS, incubated in mild hypotonic solution (0.075 M KCL/0.9% NaCl, 1:19) for 10 min at 37° C., and fixed with methanol-glacial acetic acid (3:1) for 15 min at 37° C., rinsed with distilled water and air dried. Fixed cells were stained with DAPI (2 μg/ml) for 30 min in the dark at room temperature. Cells were rinsed with PBS and distilled water, and mounted with Fluoromount-G (Southern Biotech). Micronuclei were identified based on the criteria specified by Miller at al. One thousand cells per treatment were analyzed using the fluorescence microscope.

Single Cell Gel Electrophoresis (SCGE, the Comet Assay)

The treated and control HepG2 cells embedded in 0.75% LMP (low melting point) agarose and spread on a base layer of 1% NMP (normal melting point) agarose in PBS buffer were placed in a lysis solution (2.5M NaCl, 200 mM $Na_2EDTA$, 10 mM Tris-HCl, pH10 and 1% Triton X-100) at 4° C. for 2 h. Slides were transferred to an electrophoresic box and immersed in an alkaline solution (300 mM NaOH, 1 mM $Na_2EDTA$, pH >13). After 40 min unwinding time a voltage of 25 V (300 mA) was applied for 30 min at 4° C. Slides were neutralized with 3×5 min washes with Tris-HCl (0.4 M, pH7.4), and stained with ethidium bromide (EtBr, 10 μg/ml). EtBr stained nucleotides were examined with fluorescence microscope. Total cell numbers in a field (>100) were counted and the number of nucleoids exhibiting comet tail formation was identified. Results were quantified as the number of comet nuclei out of the total number of nuclei observed from 3 independent experiments.

In Vivo Pharmacokinetic Studies

Twenty to thirty grams mice within the age of 6-8 weeks old were administrated with the indicated compounds i. v. or orally. At different time points (3, 10, 30, 60, 120, 240, 360 and 480 min), blood aliquots (300-4000 were collected in tubes coated with lithium heparin, mixed gently, then kept on ice and centrifuged at 2500×g for 15 min at 4° C., within 1 h of collection. The plasma was then harvested and kept frozen at −20° C. until further processing. For each time point, 3 mice/group were employed. The plasma samples were analyzed by HPLC.

Imdazole and Urea Derivatives

Structure-activity relationship (SAR) study shows that the catechol group in 7,8-DHF, a selective small TrkB receptor agonist, is important for agonistic activity. To improve the pharmacokinetic profiles intrinsic to catechol-containing molecules and to elevate the agonistic effect a campaign to synthesizing various bioisosteric derivatives was initiated including more imidazole or urea containing compounds (See FIG. 8C).

The compounds were subjected to in vitro ADME assays including Caco-2 permeability assay, liver microsomal stability, BBB permeability, CYP inhibition and plasma protein binding assays etc. Among these synthetic derivatives, EU-B exhibits impressive liver microsomal stability and it also potently activates TrkB receptor in primary neuronal cultures and in mouse brain after oral administration.

The in vitro ADMET profiles were analyzed. EU-B activates TrkB signalings in a dose-dependent and time-dependent manner (FIG. 12). Caco-2 permeability assay is not optimal. In order to increase the hydrophobicity, EU-B-related compounds were prepared by keeping the urea functional group. In metabilite investigation of the methylated metabolites of 7,8-DHF, it was discovered that that 7-methoxy-8-hydroxy metabolite is active. A methyl group was added on the urea group.

Synthesis of Derivatives in FIG. 9

3-acetamido-6-acetyl-2-nitrophenyl benzoate (3)

To a mixture of N-(4-acetyl-3-hydroxy-2-nitrophenyl) acetamide (1, 2.0 g, 8.4 mmol, 1.0 eq) and triethylamine (2.0 mL, 2.0 eq) in anhydrous $CH_2Cl_2$ (100 ml) was added benzoyl chloride (2, 1.2 mmol, 1.0 eq.) in portion at 0° C. Then the mixture was stirred at rt overnight. Diluted with DCM (100 mL), washed with 1N HCl (aq., 100 mL) and water (50 mL) successively. The organic phase was dried with sodium sulfate, filtered and concentrated to afford gray solid, which was purified by flash chromatography (petroleum ether-ethyl acetate. 1:1) to afford (3, 1.5 g) as a off-white solid in the yield of 52%.

$^1$H NMR (300 MHz, $CDCl_3$): δ/ppm=8.76 (s, 1H), 8.45~8.42 (dd, 1H), 8.17~8.14 (dd, 2H), 8.03~8.00 (dd, 1H), 7.68~7.65 (m, 1H), 7.55~7.50 (m, 2H), 2.54 (s, 3H), 2.23 (s, 3H), MS-ESI: cal. 342. found: 365 (M+Na).

7-amino-8-nitro-2-phenyl-4H-chromen-4-one (4)

A mixture of 3-acetamido-6-acetyl-2-nitrophenyl benzoate (3, 1.5 g, 1.0 eq.) and potassium hydroxide (0.5 g, 2.1 eq.) in pyridine (50 mL) was heated at 60° C. for 3 h and then poured into icy 1N HCl (100 mL). The yellow solid was collected and dissolved in the mixture of acetic acid (30 mL) and concentrated sulfuric acid (0.5 ml). The resulting mixture was heated at 110° C. for 2 h. The mixture was cooled to rt and poured into sodium carbonate (sat.). The yellow solid was filtered and dried in vacuo to affored (4) (0.8 g, yield: 65%)

$^1$HNMR (300 MHz, $CDCl_3$): δ/ppm=8.16~8.10 (br, 1H), 8.02~7.99 (br, 1H), 7.26~7.48 (m, 3H), 6.88~6.82 (m, 2H), 6.36 (br, 1H), MS-ESI: cal. 282. found: 283 (M+H).

7,8-diamino-2-phenyl-4H-chromen-4-one (5)

To a mixture of iron power (1.5 g, 10 eq) and $NH_4Cl$ (1.5 g, 10 eq) in ethanol-THF-water (25 ml, 2:2:1) was added 7-amino-8-nitro-2-phenyl-4H-chromen-4-one (4, 0.8 mg, 2.8 mmol) in THF (5 ml), The mixture was heated at 60° C. for 2 h. Then the solid was filtered off and the solid washed with ethyl acetate, the combined filtrate was evaporated in reduced pressure and purified by flash chromatography to afford 7,8-diamino-2-phenyl-4H-chromen-4-one (5) as a yellow solid (0.3 g) in the yield of 40%.

$^1$H NMR (300 MHz, DMSO-$d_6$): δ/ppm=7.98 (br, 2H), 7.55~7.53 (br, 1H), 7.3~77.35 (br, 1H), 6.77~6.74 (dd, 1H), 6.64 (s, 1H), 5.19~5.16 (br, 2H), 4.46~4.45 (br, 2H), MS-ESI: cal. 252. found: 253 (M+H).

2-methyl-8-phenylchromeno[7,8-d]imidazol-6(3H)-one (6)

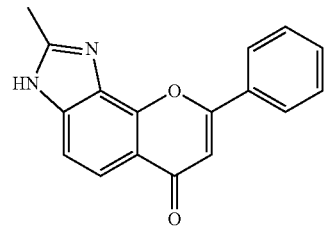 [SMILES: Cc1nc2c(ccc3c(=O)cc(-c4ccccc4)oc32)[nH]1]

A solution of 7,8-diamino-2-phenyl-4H-chromen-4-one (300 mg) in $CH_3CO_2H$ (20 mL) was heated to reflux for overnight. The volatiles were evaporated in reduced pressure and the residue partitioned between ethyl acetate/MeOH=20/1 (50 mL) and sat. sodium carbonate (25 mL). The organic phase was separated, dried with sodium sulfate, filtered and concentrated to afford yellow solid, which was recrystallized from ethyl acetate (25 mL) to afford light yellow solid (0.13 mg) in the yield of 40%.

$^1$H NMR (300 MHz, DMSO-$d_6$): δ/ppm=12.94 (br, 1H), 8.31 (br, 2H), 8.15~8.14 (m, 1H), 7.83~7.76 (br, 4H), 7.64~7.53 (m, 1H), 7.10~7.07 (br, 1H), 2.61 (s, 3H), MS-ESI: cal. 276. found: 277 (M+H).

8-phenylchromeno[8,7-d]imidazole-2,6(1H,3H)-dione (7)

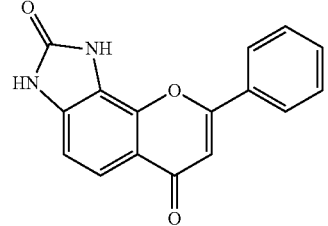 [SMILES: O=c1[nH]c2ccc3c(=O)cc(-c4ccccc4)oc3c2[nH]1]

To a solution of 7,8-diamino-2-phenyl-4H-chromen-4-one (0.3 g, 1.0 eq) in anhydrous THF (50 ml) was added CDI (2.4 g, 10 eq), then the mixture was refluxed for overnight. The solution was removed in vacuo, cooked with ethyl acetate and the product was collected by filtration, washed with ethyl acetate and dried to yield 0.25 g of product as light yellow solid in the yield of 75%.

$^1$H NMR (300 MHz, DMSO-$d_6$): δ/ppm=11.89 (br, 1H), 11.31 (br, 1H), 8.29~8.26 (br, 2H), 7.62~7.52 (m, 4H), 7.07~7.04 (br, 1H), 6.97 (s, 1H), MS-ESI: cal. 278. found: 279 (M+H).

Synthesis of Derivatives in FIG. 10

4-(benzyl(methyl)amino)-3,5-difluorobenzoate (3)

To a mixture of N-(4-acetyl-3-hydroxy-2-nitrophenyl) acetamide (1, 3.0 g, 12.6 mmol, 1.0 eq) and triethylamine (8.0 mL, 4.0 eq) in anhydrous $CH_2Cl_2$ (50 ml) was added 4-(benzyl(methyl)amino)-3,5-difluorobenzoyl chloride (2, 6.0 g, 18.05 mmol, 1.5 eq.) in portion at 0° C. Then the mixture was stirred at rt for overnight. Diluted with DCM (100 mL), washed with 1N HCl (100 mL) and water (50 mL). The organic phase was separated, dried with sodium sulfate, filtered and concentrated to afford gray solid, which was purified by flash chromatography (petroleum ether/ethyl acetate=1/1) to afford (3, 1.5 g, 24%).

$^1$H NMR (300 MHz, $CDCl_3$): δ/ppm=8.71 (br, 1H), 8.51~8.48 (m, 1H), 8.02~7.99 (m, 1H), 7.63~7.59 (m, 2H), 7.34~7.25 (m, 5H), 4.42 (s, 2H), 2.92 (s, 3H), 2.53 (s, 3H), 2.22 (s, 3H), MS-ESI: cal. 497. found: 498 (M+H), 520 (M+Na).

7-amino-2-(4-(benzyl)methyl)amino)-3,5-difluorophenyl)-8-nitro-4H-chromen-4-one (4)

A mixture of 4-(benzyl(methyl)amino)-3,5-difluorobenzoate (3, 1.5 g, 1.0 eq.) and potassium hydroxide (0.5 g, 2.1 eq.) in pyridine (50 mL) was heated to 60° C. for 3 h and poured into icy 1N HCl (100 mL). The yellow solid was collected and dissolved in acetic acid (30 mL) and concentrated sulfuric acid (0.5 ml. The resulting mixture was heated to 110° C. for 2 h. The mixture was cooled to rt and poured into sat.sodium carbonate. The yellow solid was filtered and dried in vacuo to afford (4) (0.8 g, yield: 60%)

$^1$H NMR (300 MHz, $CDCl_3$): δ/ppm=8.28 (br, 1H), 7.49 (m, 1H), 7.37~7.36 (m, 5H), 7.29 (m, 1H), 6.88~6.72 (m, 1H), 6.48 (br, 1H), 4.42 (br, 2H), 2.95 (s, 3H), MS-ESI: cal. 437. found: 438 (M+H).

7,8-diamino-2-(4-(benzyl)methyl)amino)-3,5-difluorophenyl)-4H-chromen-4-one (5)

To a suspension of iron power (1.5 g, 10.eq) and $NH_4Cl$ (1.5 g, 10 eq) in 2:2:1 ethanol-THF-water (25 ml) was added 7-amino-2-(4-(benzyl(methyl)amino)-3,5-difluorophenyl)-8-nitro-4H-chromen-4-one (4, 0.8 mg, 2.8 mmol) in THF (5 ml), The mixture was heated at 60° C. for 2 h. Then the solid was filtered and washed with ethyl acetate, the filtrate was evaporated under reduced pressure and purified by flash chromatography to afford 7,8-diamino-2-(4-(benzyl(methyl)amino)-3,5-difluorophenyl)-4H-chromen-4-one e (5) as a yellow solid (0.2 g, yield: 27%).

$^1$H NMR (300 MHz, $CDCl_3$): δ/ppm=7.4~77.46 (br, 1H), 7.3~67.34 (m, 6H), 6.97~6.80 (br, 2H), 6.56 (s, 1H), 4.38 (s, 2H), 2.92 (s, 3H), MS-ESI: cal. 407. found: 408 (M+H).

8-(4-(benzyl)methyl)amino)-3,5-difluorophenyl)chromeno[8,7-d]imidazole-2,6(1H,3H)-dione (6)

To a solution of 7,8-diamino-2-(4-(benzyl(methyl)amino)-3,5-difluorophenyl)-4H-chromen-4-one (0.2 g, 1.0 eq) in anhydrous THF (50 ml) was added CDI (2.4 g, 10 eq), then the mixture was refluxed for overnight. The solution was removed in vacuo, cooked with ethyl acetate and the product was collected by filtration, washed with ethyl acetate and dried to yield 0.20 g (91% yield) of product as light yellow solid.

$^1$H NMR (300 MHz, DMSO-$d_6$): δ/ppm=11.96 (br, 1H), 11.29 (br, 1H), 8.03~7.97 (br, 1H), 7.58~7.53 (br, 1H), 7.33~7.19 (br, 5H), 7.06~6.96 (br, 3H), 4.32~4.29 (br, 2H), 2.85~2.79 (br, 3H), MS-ESI: cal. 433. found: 434 (M+H).

8-(3,5-difluoro-4-(methylamino)phenyl)chromeno[8,7-d]imidazole-2,6(1H,3H)-dione (7)

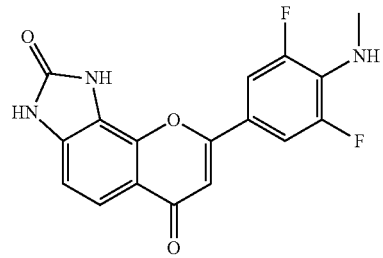 [SMILES: CNc1c(F)cc(-c2cc(=O)c3ccc4[nH]c(=O)[nH]c4c3o2)cc1F]

A solution of 8-(4-(benzyl(methyl)amino)-3,5-difluorophenyl)chromeno [8,7-d]imidazole-2,6(1H,3H)-dione (6, 0.2 g, 2.77 mmol) and 10% Pd/C (0.2 g) in the mixture solution of DMF (300 mL) and MeOH (100 ml) was stirred at the atmosphere of hydrogen overnight. The solid was filtered and the filtrate was evaporated in reduced pressure to afford 8-(3,5-difluoro-4-(methylamino)phenyl)chromeno[8,7-d]imidazole-2,6(1H,3H)-dione (7) as a light yellow solid (0.12 g, yield: 75%).

$^1$H NMR (300 MHz, DMSO-$d_6$): δ/ppm=11.96 (br, 1H), 11.31 (br, 1H), 8.00~7.98 (br, 2H), 7.62~7.59 (br, 1H), 7.08~7.06 (br, 1H), 6.89 (br, 1H), 6.07 (br, 1H), 3.02 (br, 3H), MS-ESI: cal. 343. found: 344 (M+H).

Synthesis of Derivative in FIG. 11

3-acetamido-6-acetyl-2-nitrophenyl 4-(dimethylamino)-3,5-difluorobenzoate (3)

To a mixture of N-(4-acetyl-3-hydroxy-2-nitrophenyl)acetamide (1, 1.2 g, 5.0 mmol, 1.0 eq) and triethylamine (8.0 mL, 4.0 eq) in anhydrous $CH_2Cl_2$ (50 ml) was added 4-(dimethylamino)-3,5-difluorobenzoyl chloride (2, 6.0 g hydrochloride, 24.8 mmol, 1.5 eq.) in portion at 0° C. Then the mixture was stirred at rt for overnight. Diluted with DCM (100 mL), washed with 1N HCl (100 mL) and water (50 mL). The organic phase was separated, dried with sodium sulfate, filtered and concentrated to afford gray solid, which was purified by flash chromatography (petroleum ether/ethyl acetate=1/1) to afford (3, 1.5 g, 59.6%).

$^1$H NMR (300 MHz, $CDCl_3$): δ/ppm=10.60 (br, 1H), 8.79~8.77 (br, 2H), 7.64~7.59 (br, 2H), 3.06~3.05 (s, 6H), 2.56 (s, 3H), 2.33 (s, 3H), MS-ESI: cal. 421. found: 444 (M+Na).

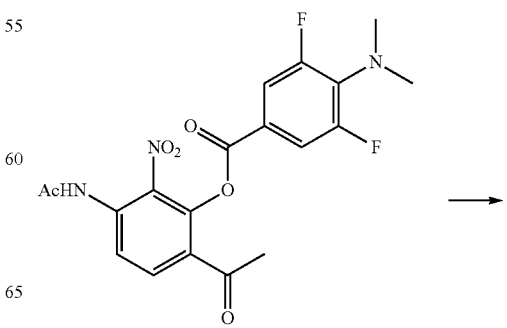

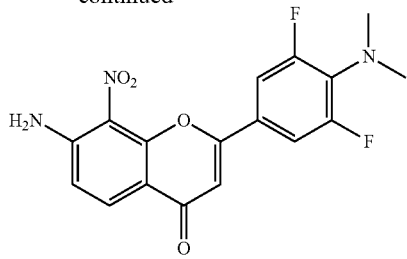

7-amino-2-(4-(dimethylamino)-3,5-difluorophenyl)-8-nitro-4H-chromen-4-one (4)

A mixture of 3-acetamido-6-acetyl-2-nitrophenyl4-(dimethylamino)-3,5-difluorobenzoate (3, 1.5 g, 1.0 eq.) and potassium hydroxide (0.4 g, 2.1 eq.) in pyridine (50 mL) was heated to 60° C. for 3 h and poured into icy 1N HCl (100 mL). The yellow solid was collected and dissolved in acetic acid (30 mL) and concentrated sulfuric acid (0.5 ml. The resulting mixture was heated to 110° C. for 2 h. The mixture was cooled to rt and poured into sat. sodium carbonate. The yellow solid was filtered and dried in vacuo to afforded (4) (0.8 g, yield: 62%)

$^1$H NMR (300 MHz, DMSO-d$_6$): δ/ppm=7.84~7.76 (br, 3H), 7.63~7.59 (m, 2H), 6.96~6.90 (m, 2H), 2.89 (s, 6H). MS-ESI: cal. 361. found: 362 (M+H).

7,8-diamino-2-(4-(dimethylamino)-3,5-difluorophenyl)-4H-chromen-4-one (5)

To a suspension of iron power (1.5 g, 10.eq) and NH$_4$Cl (1.5 g, 10 eq) in 2:2:1 ethanol-THF-water (25 ml) was added 7-amino-2-(4-(dimethylamino)-3,5-difluorophenyl)-8-nitro-4H-chromen-4-one (4, 0.8 mg, 2.2 mmol) in THF (5 ml), The mixture was heated at 60° C. for 2 h. Then the solid was filtered and washed with ethyl acetate, the filtrate was evaporated in reduced pressure and purified by flash chromatography to afford 7,8-diamino-2-(4-(dimethylamino)-3,5-difluorophenyl)-4H-chromen-4-one (5) as a yellow solid (0.3 g, yield: 40%).

MS-ESI: cal. 331. found: 332 (M+H).

8-(4-(dimethylamino)-3,5-difluorophenyl)chromeno[8,7-d]imidazole-2,6(1H,3H)-dione (6)

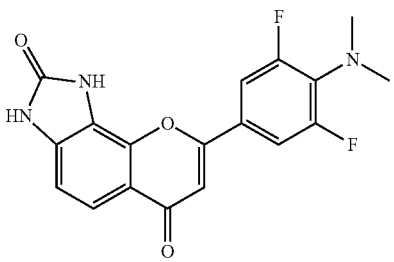 [SMILES: CN(C)c1c(F)cc(-c2cc(=O)c3ccc4[nH]c(=O)[nH]c4c3o2)cc1F]

To a solution of 7,8-diamino-2-(4-(dimethylamino)-3,5-difluorophenyl)-4H-chromen-4-one (5) (0.3 g, 1.0 eq) in anhydrous THF (50 ml) was added CDI (2.4 g, 10 eq), then the mixture was refluxed for overnight. The solution was removed in vacuo, cooked with ethyl acetate and the product was collected by filtration, washed with ethyl acetate and dried to yield 0.25 g (77% yield) of product as light yellow solid.

$^1$H NMR (300 MHz, DMSO-d$_6$): δ/ppm=11.99 (br, 1H), 11.34 (br, 1H), 8.07~8.04 (br, 2H), 7.63~7.61 (br, 1H), 7.09~7.02 (br, 2H), 2.95 (s, 6H), MS-ESI: cal. 357. found: 358 (M+H).

The invention claimed is:
1. A compound having Formula I:

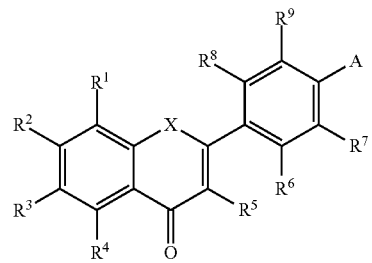

Formula I or salt thereof wherein,
X is O;
A is pyrrolidinyl;
$R^1$ and $R^2$ and attached atoms form a 5 membered heterocyclic ring optionally substituted with $R^{15}$;
$R^3$, $R^4$, $R^5$, $R^6$, and $R^8$, are hydrogen
$R^7$ and $R^9$ are halogen; and
$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and
$R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound of claim 1, wherein $R^1$ and $R^2$ form imidazolyl or indolyl.

3. A compound having Formula IA

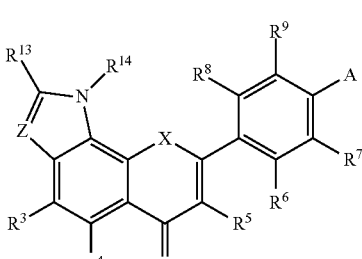

Formula IA or salt thereof wherein
X is O;
A is amino, aminoalkyl, diaminoalkyl, or heterocyclyl;
Z is N or CH;

$R^{13}$ is hydroxy or alkyl optionally substituted with one or more, the same or different, $R^{15}$;

$R^3$, $R^4$, $R^5$, $R^6$, $R^8$, and $R^{14}$ are hydrogen $R^7$ and $R^9$ are halogen;

$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

4. The compound of claim 1 wherein the compound is selected from:

8-(3,5-difluoro-4-(pyrrolidin-1-yl)phenyl)-2-methyl-chromeno[7,8-d]imidazol-6(3H)-one, 2-chloro-8-(3,5-difluoro-4-(pyrrolidin-1-yl)phenyl)chromeno[7,8-d]imidazol-6(3H)-one, and 8-(3,5-difluoro-4-(pyrrolidin-1-yl)phenyl)chromeno[7,8-d]imidazole-2,6(1H,3H)-dione or salts thereof.

* * * * *